United States Patent
Chinowsky et al.

(10) Patent No.: US 7,675,624 B2
(45) Date of Patent: Mar. 9, 2010

(54) PORTABLE AND CARTRIDGE-BASED SURFACE PLASMON RESONANCE SENSING SYSTEMS

(75) Inventors: Timothy M. Chinowsky, Seattle, WA (US); Scott D. Soelberg, Seattle, WA (US); Peter C. Kauffman, Bainbridge Island, WA (US); Clement E. Furlong, Bainbridge Island, WA (US); Jared Tritz, Seattle, WA (US); Michael S. Grow, Bothell, WA (US); Alexei N. Naimushin, Bellevue, WA (US); Sinclair S. Yee, Seattle, WA (US)

(73) Assignee: University of Washington, Seattle, WA (US)

( * ) Notice: Subject to any disclaimer, the term of this patent is extended or adjusted under 35 U.S.C. 154(b) by 533 days.

(21) Appl. No.: 11/398,964

(22) Filed: Apr. 5, 2006

(65) Prior Publication Data

US 2006/0279737 A1 Dec. 14, 2006

Related U.S. Application Data

(60) Provisional application No. 60/671,731, filed on Apr. 15, 2005.

(51) Int. Cl.
*G01N 21/55* (2006.01)
(52) U.S. Cl. ...................................... 356/445
(58) Field of Classification Search ......... 356/445–448, 356/244–246
See application file for complete search history.

(56) References Cited

U.S. PATENT DOCUMENTS

| | | | |
|---|---|---|---|
| 5,912,456 A | 6/1999 | Melendez et al. | 250/216 |
| 6,326,612 B1 | 12/2001 | Elkind et al. | 250/239 |
| 7,148,968 B2 * | 12/2006 | Codner et al. | 356/445 |
| 2004/0086872 A1 | 5/2004 | Childers et al. | 435/6 |
| 2004/0201848 A1 | 10/2004 | Codner et al. | 356/445 |
| 2004/0224362 A1 | 11/2004 | Gjerde et al. | 435/7.1 |

(Continued)

OTHER PUBLICATIONS

Bain, C., "Formation of two-component surfaces by the spontaneous assembly of monolayers on gold from solutions containing mixtures of organic thiols," *J Am Chem Soc*, 1988, 110: 6560-6561.

(Continued)

*Primary Examiner*—Michael P Stafira
(74) *Attorney, Agent, or Firm*—Woodcock Washburn LLP

(57) ABSTRACT

This specification discloses various improvements in the field of SPR sensing systems. One improvement relates to a portable SPR sensing system, e.g., a system contained within a suitcase that can be hand-carried to a monitoring site. Another improvement relates to a portable, cartridge-based SPR sensing system. In this system, selected portions of the system's electrical and fluidics systems are allocated between a base unit and a removable/disposable cartridge. Other improvements relate to methods or protocols for operating an SPR sensing system. Such methods provide for the elimination of false positives and increased sensitivity, e.g., by using secondary antibodies with specificity for different target epitopes and by sensor element redundancy. In addition, protocols are provided for the detection of small molecules. Such protocols may employ a competition type assay where the presence of the analyte inhibits the binding of antibodies to surface immobilized analyte, or a displacement assay, where antibodies bound to the analyte on the sensor surface are displaced by free analyte.

62 Claims, 22 Drawing Sheets

U.S. PATENT DOCUMENTS

2005/0045543 A1     3/2005     Gjerde et al. ............ 210/198.2
2005/0084893 A1*    4/2005     Herman et al. ................ 435/6

OTHER PUBLICATIONS

Bokken et al., "Immunochemical detection of *Salmonella* group B, D and E using an optical surface plasmon resonance biosensor," *FEMS Microbiol Lett*, 2003, 222(1): 75-82.

Boltovets, P.N.M. et al., "Simple method for plant virus detection: effect of antibody immobilization technique," *J Virol Methods*, 2002, 105(1): 141-146.

Brown, S., "Metal-recognition by repeating polypeptides," *Nat Biotechnol*, 1997, 15:269-272.

Chinowsky, T.M. et al., "Performance of Spreeta 2000 integrated surface plasmon resonance affinity sensor," *Sens Acuators*, 2003, B91: 266-274.

Elkind, J.L. et al., "Integrated analytical sensors: the use of the TISPR-1 as a biosensor," *Sens Actuators-B*, 1999, 54: 182-190.

He, L. et al., "Colloidal Au-enhanced surface plasmon resonance for ultrasenstive detection of DNA hybridization," *J Am Chem Soc*, 2000, 122: 9071-9077.

Kooyman, "The use of self-assembled receptor layers in immunosensors," *Thin Solid Films*, 1994, 244: 913-916.

Ktretschmann, E. et al., "The determination of the Optical Constants of Metals by Excitation of Surface Plasmons," *Z Physik*, 1971, 241: 313-24.

Li, Z.L. et al., "Identification of c-Jun as bci-2 transcription factor in human uterine endometrium," *The J Histochem Cytochem*, 2003, 51(12): 1601-1609.

Melendez, J. et al., "A commercial solution for surface plasmon sensing," *Sens Acuators*, 1996, B B35: 212-216.

Melendez, J. et al., "Development of a surface plasmon resonance sensor for commercial applications," *Sens Actuators*, 1997, B B39: 375-79.

Mullet, W.M. et al., "Surface plasmon resonance-based immunoassays," *Methods*, 2000, 22(1): 77-91.

Naimushin et al., "Airborne analyte detection with an aircraft-adapted surface plasmon resonance (SPR) sensor system," 2005, *Sens Actuators*, vol. 104 pp. 237-248.

Naimushin et al., "A portable surface plasmon resonance (SPR) sensor system with temperature regulation," 2003, *Sens Acuators, B* 96: 253-260.

Naimushin et al., "Detection of *Staphlococcus aureus* enteriotoxin B in femtomolar amounts by a miniature integrated two-channel SPR sensor," 2002, *Biosens Bioelectron*, 17: 573-584.

Savran, C.A. et al., "Micromechanical Detection of Proteins Using Aptamer-Based Receptor Molecules," *Anal Chem*, 2004, 76(11): 3194-3198.

Strong, A. et al., "Detection of trinitroluene (TNT) extracted from soil using a surface plasmon resonance (SPR)—based sensor platform," *SPIE—The International Society for Optical Engineering, Aerosense XIII, Proceedings*, Sep. 1999.

Woodbury, R.G. et al., "Construction of surface plasmon resononace biosensors using a gold-binding polypeptide and a miniature integrated sensor," *Bionsens Bioelectron*, 1998, 13: 1117-1126.

Davies, J. et al., "Surface Plasmon Resonance — Theory and Experimental Considerations," *Surface Analytical Techniques for Probing Biomaterial Processes*, CRC Press, NY, 1996, Ch. 3, 67-130.

Biacore AB, BIACORE® 2000 Instrument Handout, 1999, 1-352.

* cited by examiner

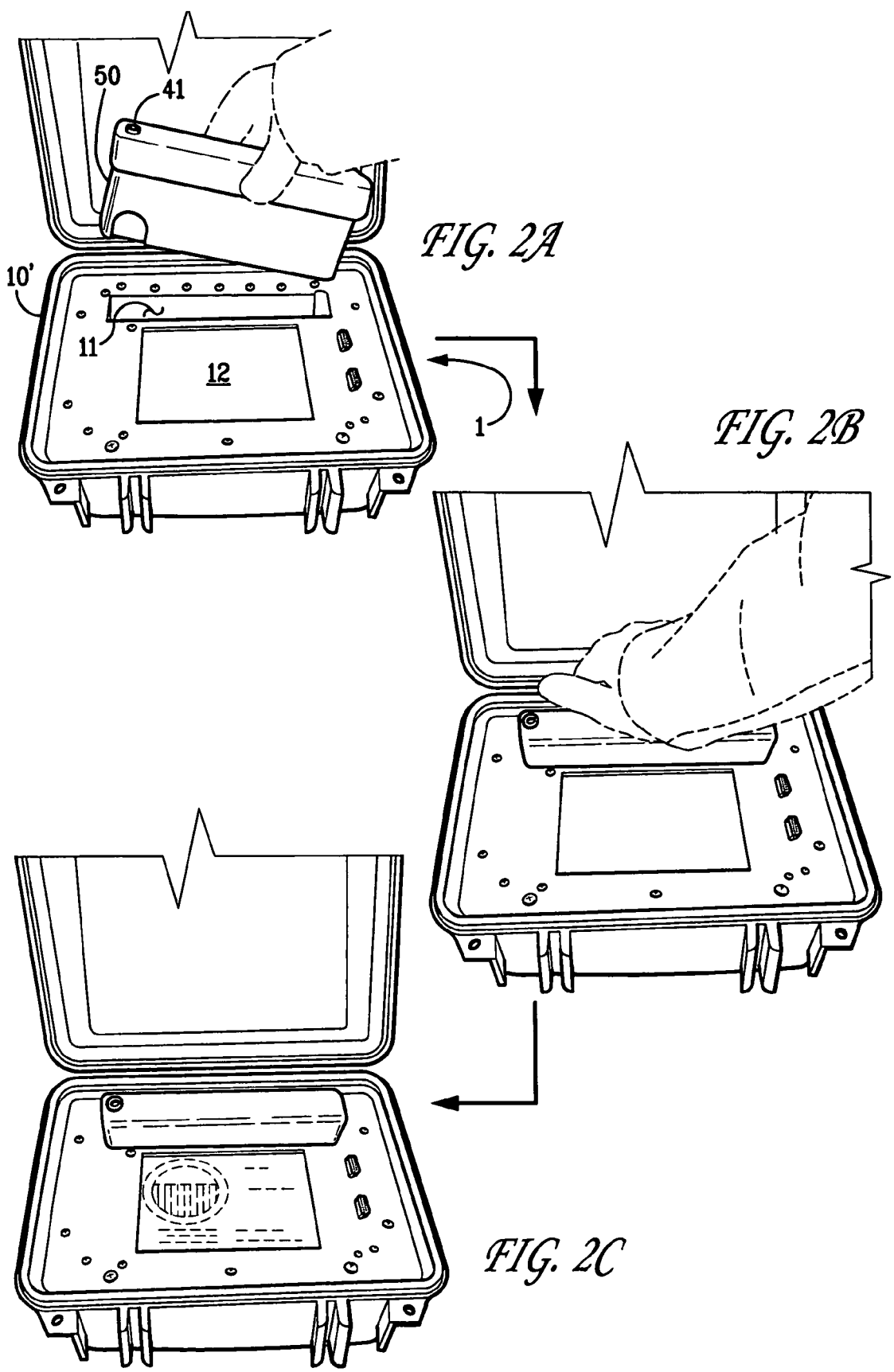

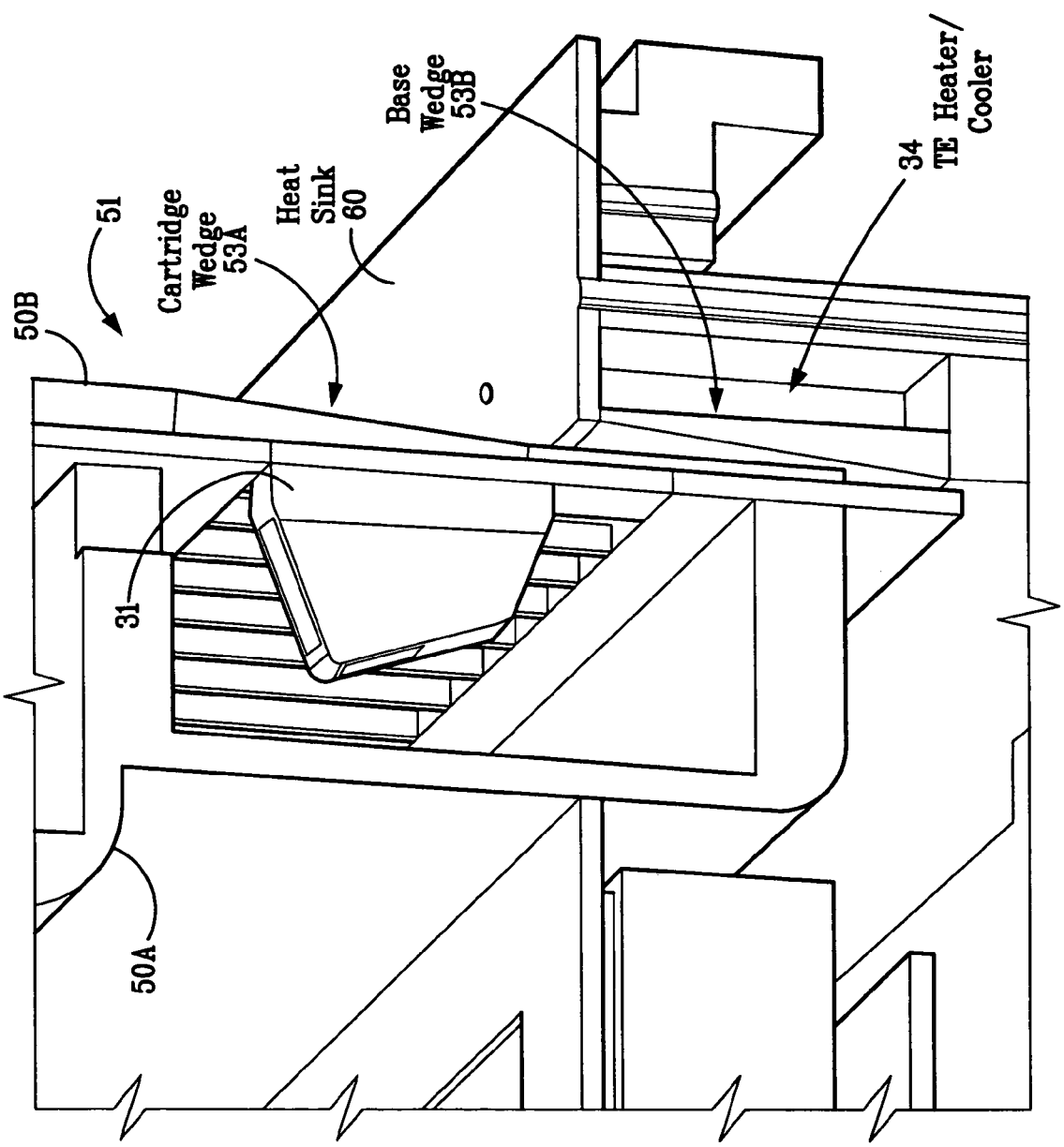

PORTABLE AND CARTRIDGE-BASED SURFACE PLASMON RESONANCE SENSING SYSTEMS

CROSS REFERENCE TO RELATED APPLICATIONS

The present application claims the benefit of U.S. Provisional Patent Application No. 60/671,731, filed Apr. 15, 2005, which is hereby incorporated by reference in its entirety.

STATEMENT REGARDING FEDERALLY SPONSORED RESEARCH

The subject matter described herein was funded through a grant by the United States Department of Defense, under DAAD13-03-C-0024 and DAAD13-99-C-0032, "Optimization and Fabrication of a Multichannel SPR System for Detection of Biological and Chemical Agents," and the United States Government has certain rights therein.

FIELD OF THE INVENTION

The present invention relates generally to surface plasmon resonance (SPR) sensing systems, and more particularly to improvements in such systems. Still more particularly, the present invention relates to portable SPR sensing systems, including but not limited to a cartridge-based system, for detecting biological and chemical agents.

BACKGROUND OF THE INVENTION

There are many environmental applications for biosensors that can provide real-time analyses. For example, one of the most pressing current needs is monitoring for agents of chemical and bioterrorism. These applications require systems that can rapidly detect small organics including nerve agents, toxic proteins, viruses, spores and whole microbes. A second area of application is monitoring for environmental pollutants. Processing of grab samples through chemical laboratories requires significant time delays in the analyses, preventing the rapid mapping and cleanup of chemical spills. The current state of development of miniaturized, integrated SPR sensor elements has allowed for the development of inexpensive, portable biosensor systems capable of the simultaneous analysis of multiple analytes. Most of the detection protocols make use of antibodies immobilized on the sensor surface. For example, the Spreeta 2000 SPR biosensor elements manufactured by Texas Instruments Corporation provide multiple channels for each sensor element in the system. (See, e.g., documents cited in our Information Disclosure Statement and U.S. Pat. No. 5,912,456, Jun. 15, 1997, "Integrally Formed Surface Plasmon Resonance Sensor".)

SPR biosensors are based on the fundamental Kretschmann design where the intensity of transverse magnetic (TM) polarized light reflected off a thin layer of gold (~50 nm) on the surface of a prism shows a dependence on the angle of incidence or wavelength of the incident light. See, e.g., Kretschmann E, *The determination of the Optical Constants of Metals by Excitation of Surface Plasmons*, Z Physik 241:313-324 (1971). A plot of the intensity of reflection against the angle of reflection produces an SPR curve or profile. A minimum in the SPR curve is observed when the frequency and momentum of the incident light are matched with that of the surface plasmons, at which point the energy is absorbed by the surface plasmons (and not reflected). The angle or wavelength at which the minimum of reflection occurs is dependent on the refractive index (RI) of the medium in contact with the outside of the gold layer. Attachment of specific recognition elements on the gold surface (usually antibodies) and passivation of the gold surface to non-specific binding provides a condition for monitoring for the presence of specific targets in real-time. Since the refractive index of protein (RI~1.45) is greater than that of usual aqueous buffers (RI~1.334), when an analyte of refractive index greater than that of water/buffer and of sufficient size is bound at the surface, the refractive index change is sufficient to result in a change in the position of the minimum of the SPR curve. Instrumentation software can convert the change in SPR minima into refractive index as a function of time, thus allowing the binding event to be analyzed in real time. See, e.g., Davies J. (ed), *Surface analytical techniques for probing biomaterial processes*, CRC Press, NY (1996).

The first commercial instruments available were both large and expensive and thus not suitable for applications that required portability. Recent advances in miniaturization of SPR technology have made possible the development of portable systems that are adaptable to many different uses. See, Naimushin, et al., *Detection of Staphlococcus aureus enterotoxin B in femtomolar amounts by a miniature integrated two-channel SPR sensor*, Biosens Bioelectron 17:573-584 (2002); and Naimushin, et al., *A portable surface plasmon resonance (SPR) sensor system with temperature regulation*, Sens Actuators B 96:253-260 (2003). Such uses include but are not limited to: 1) continuous monitoring of water systems; 2) continuous monitoring of air supply systems, when coupled with a sample collection device that transfers analytes into the aqueous phase; 3) rapid identification of possible agents of chemical or biological warfare; 4) general laboratory analyses of intermolecular interactions, e.g., protein/protein interactions, protein/ligand interactions, and protein/nucleic acid interactions; 4) environmental monitoring; 5) drug discovery; 6) in-office diagnostics; 7) in-emergency-vehicle analyses, e.g., rapid detection of plasma levels of cardiac enzyme levels, and 8) automating protein purification protocols.

SUMMARY OF THE INVENTION

This specification discloses various improvements in the field of SPR sensing systems. One improvement relates to a portable SPR sensing system, e.g., a system contained within a suitcase that can be hand-carried to a monitoring site.

Another improvement relates to a portable, cartridge-based SPR sensing system. In this system, selected portions of the system's electrical and fluidics systems are allocated between a base unit and a removable/disposable cartridge.

Other improvements described herein relate to methods or protocols for operating an SPR sensing system. Such methods provide for the elimination of false positives and increased sensitivity, e.g., by using secondary antibodies with specificity for different target epitopes and by sensor element redundancy. In addition, protocols are provided for the detection of small molecules. Such protocols may employ a competition type assay where the presence of the analyte inhibits the binding of antibodies to surface immobilized analyte, or a displacement assay, where antibodies bound to the analyte on the sensor surface are displaced by free analyte.

Other aspects of the present invention are described below.

BRIEF DESCRIPTION OF THE DRAWINGS

FIGS. 2A, 2B and 2C depict illustrative embodiment of a portable, cartridge-based SPR sensing system in accordance with the present invention.

FIG. 4 depicts a portion of the cartridge housing, including the structure for mounting a plurality of SPR sensors, and a wedge portion of a mating means for mating a heat sink with a base unit heater cooler.

DETAILED DESCRIPTION OF ILLUSTRATIVE EMBODIMENTS

In the following sections we first provide a brief overview of basic technology underlying SPR sensing systems in accordance with the present invention, and in the two sections following the overview we describe illustrative embodiments containing various inventive features. The illustrative embodiments include a cartridge-based SPR sensing system and a portable SPR sensing system.

A. Overview

Figure 1A:
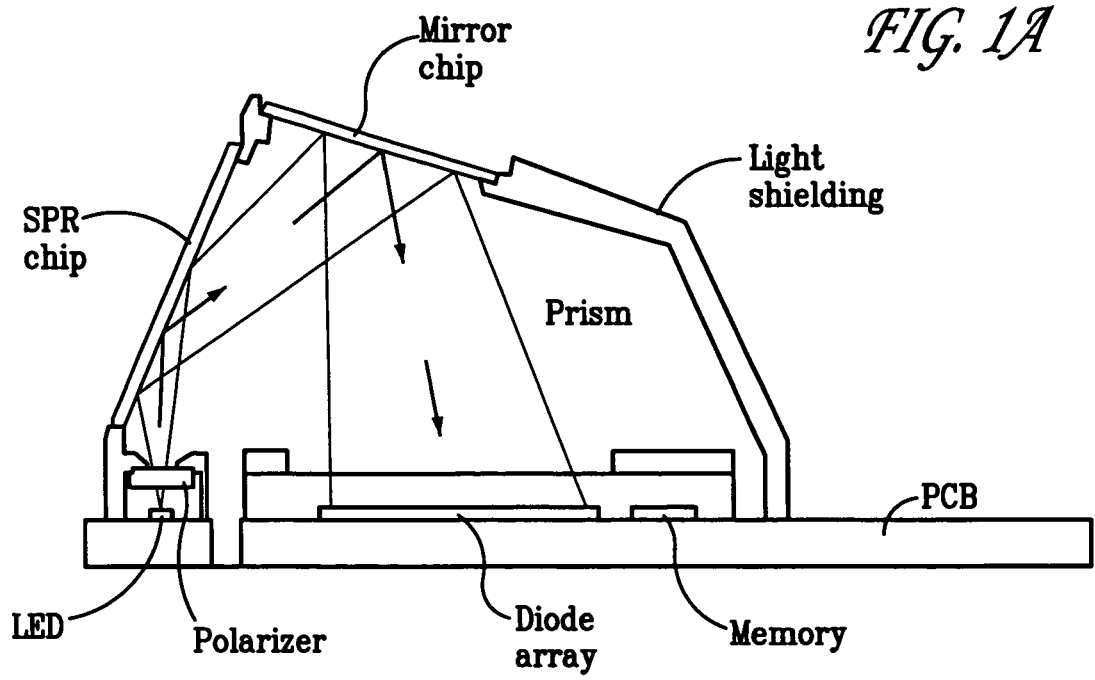
FIG. 1A schematically depicts an illustrative Spreeta sensor.

An illustrative Spreeta sensor is shown schematically in FIG. 1A. This sensor is a miniaturized SPR sensor approximately one inch in the longest dimension. The internals of the sensor include approximately fifty nanometers of gold deposited on a small glass substrate glued to the Spreeta front with the gold side facing out to form the SPR chip. The gold thus exposed forms the sensing surface. Inside, a transparent substrate fills the volume of the sensor. Beneath the substrate, embedded in the sensor, is an LED positioned to illuminate the gold from the inside over a range of angles. The light reflected from the gold is directed by a mirror chip to a photodiode array embedded inside the sensor. The photodiode array captures the light at each of one hundred and twenty-eight (128) unique angles of reflection.

Figure 1B:
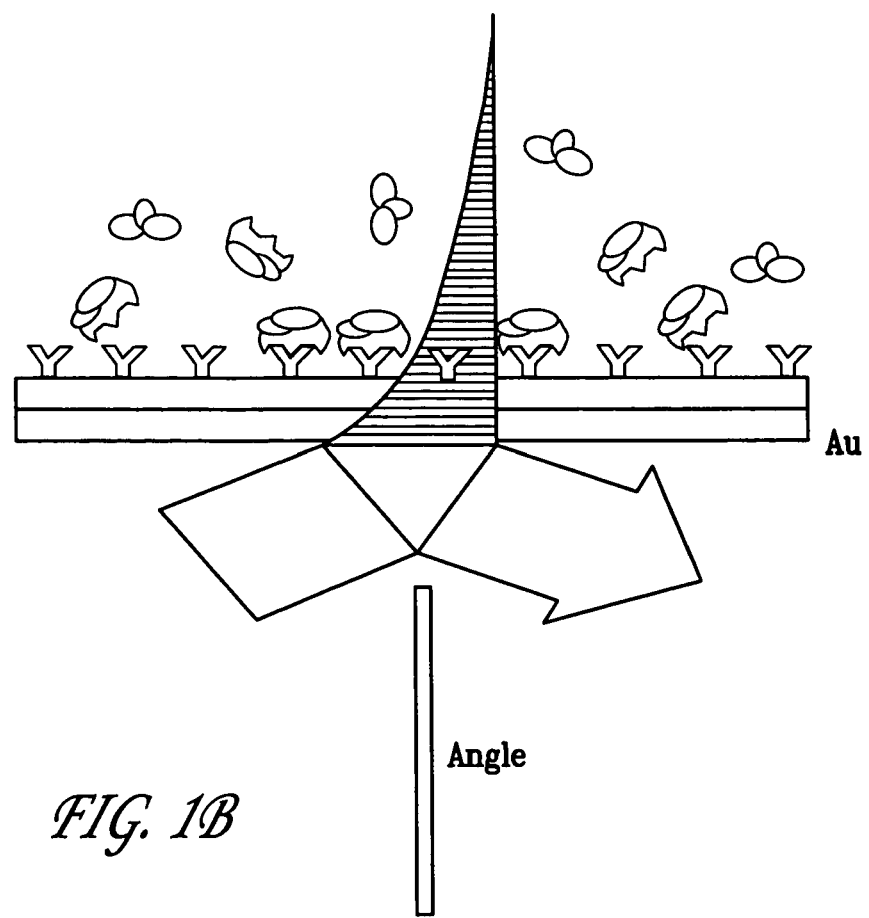
FIGS. 1B and 1C show how binding events can be detected from the sensor data.
Figure 1C:
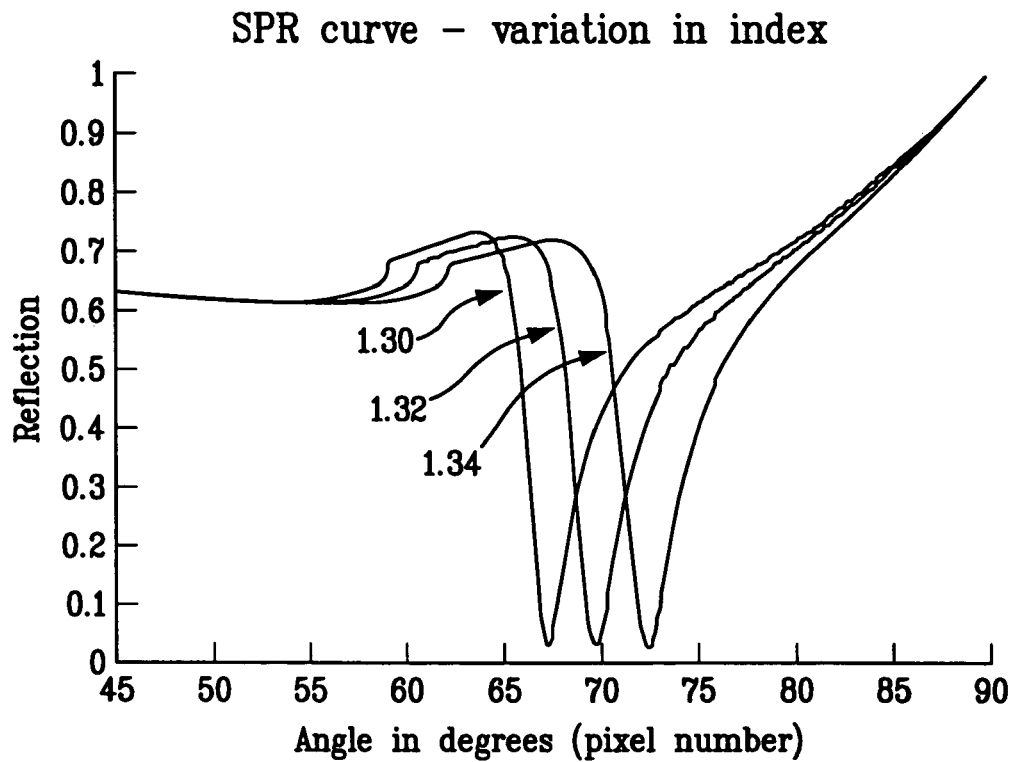

FIGS. 1B and 1C illustrate how binding events can be detected from the sensor data. FIG. 1B illustrates that reagents bind to the sensor surface changing the index of refraction, and that the amount of light collected at each angle shifts as the index of refraction changes. To use the Spreeta sensor as a detector for specific chemical or biological agents, the gold sensing surface can be coated with a monolayer or matrix of antibodies. The antibodies are depicted in FIG. 1B with a "Y" shape. As sample reagent flows across the sensor surface, an analyte specific to the antibody (if present) will bind near the gold surface and thus change the refractive index in this region. The change in refractive index will be proportional to the amount of bound analyte.

Refractive index values may then be obtained from the Spreeta sensor data. Since each photodiode in the array corresponds to a unique angle of incidence for the light that travels from the LED along a path that reflects the light from the surface plasmon layer, light levels shift in accordance with refractive index change of the sample region as a function of angle. The manner in which light levels shift as a function of angle with refractive index is illustrated FIG. 1C. The dip in the reflection spectrum can be used to identify the changing refractive index.

For a given sample refractive index value, a subset of angles will register distinctly lowered power values generating dips in the SPR curve. This is because at or near the resonance angle most of the light energy is actually coupling into the surface plasmon wave at the sensor surface and thus never reaches the photodiode. One way of resolving the information in an SPR curve would be to simply choose the pixel value registering the lowest light level. Another way would be to choose a subset of pixels neighboring the pixel with lowest light levels and find a weighted average of those values below a baseline. It should be noted that the specific index of refraction value is not usually of primary interest because the Spreeta sensor is typically used as a differential sensor. Simply resolving the shift in index of refraction is enough to provide information about binding events.

Since the index of refraction for solutions of interest are temperature dependent, it is beneficial to ensure that thermal fluctuations do not occur since they could be confused with a binding event. In an illustrative embodiment of the present invention, a control goal is to stabilize the temperature of the sensor and sample to within a tenth of a degree for the duration of assay, or about three hundred seconds.

As explained in greater detail below, the Spreeta sensor may be utilized in a portable instrument, in accordance with an illustrative embodiment of the present invention. Functionally, each sensor has three regions of sensitivity on its surface, and each of these can be functionalized with a unique antibody. By placing eight sensors in the instrument, a total of twenty-four (24) agents can be monitored during a single assay. The present invention is of course not limited to this particular configuration, and could be embodied in a system have more or fewer than twenty-four channels.

Figure 1D:
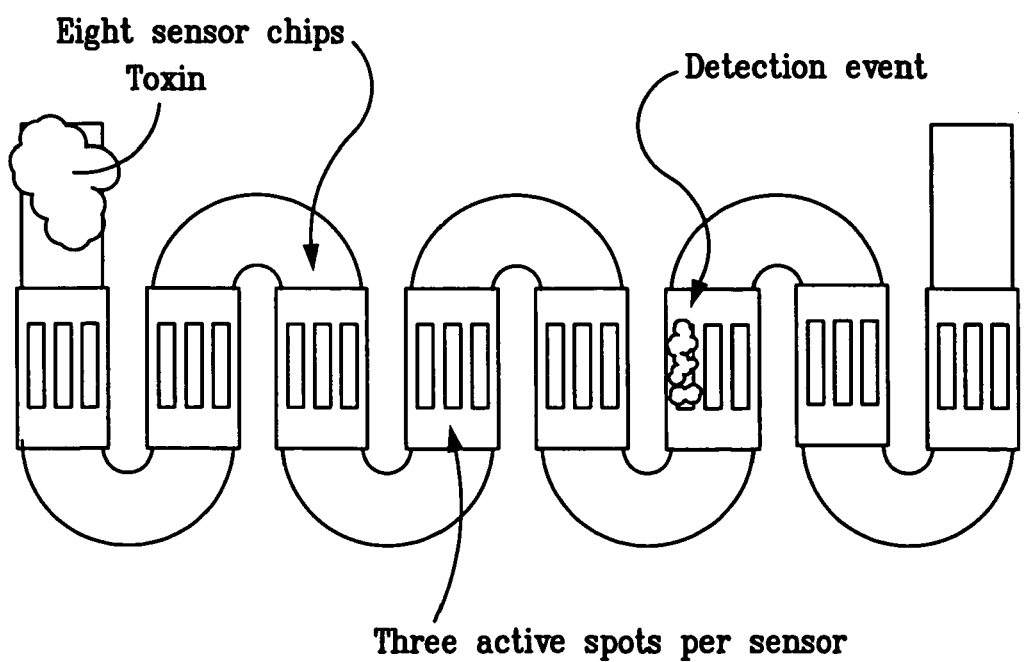
FIG. 1D schematically depicts an instrument configuration in which toxin exits after following a path that brings the toxin into contact with each of the eight sensors.

FIG. 1D schematically depicts an instrument configuration in which toxin exits after following a path that brings the toxin into contact with each of the eight sensors. In this illustration, the third sensor from left has bound some of the toxin to its leftmost sensitive region, thus indicating a "detection event."

The array of eight sensors and other fluidic components (described below) may be part of a disposable sensing cartridge, which keeps liquid separate from the electronics and is designed to be inserted into a base unit containing electronics, which in turn read data from the sensor array inside the cartridge. The base unit supplies electrical power and control signals to the sensors. It also provides a peristaltic pumping interface to meter the movement of fluid while valve switching and fluidics routing are handled inside the cartridge.

We will now describe two presently preferred embodiments employing various inventive features. The first embodiment is a portable, cartridge-based SPR sensing system, and the second embodiment is a portable SPR sensing system.

B. Cartridge-Based SPR Sensing System

1. Introduction

An illustrative embodiment of a portable, cartridge-based SPR sensing system 1 is depicted in FIGS. 2A, 2B and 2C. The system 1 includes a portable base unit housing 10' and a disposable cartridge 50 constructed to be removably mated with the housing. In addition, the system includes a base unit electrical system (not shown) contained within the base unit housing; a cartridge electrical system contained within the cartridge (not shown); a base unit fluidics system (not shown) contained within the base unit housing; and a cartridge fluidics system contained within the cartridge (not shown). The base unit and cartridge electrical and fluidics systems are arranged as described below and depicted in the following drawings figures (e.g., see FIGS. 2-14) for detecting the presence of predefined agents in a fluid medium using SPR.

As shown in FIG. 2A, the cartridge-based system also includes a slot 11 into which the cartridge 50 may be inserted for mating with the base unit 10', a display 12, and an injection port 41 for injecting sample materials into the cartridge.

Figure 3A:
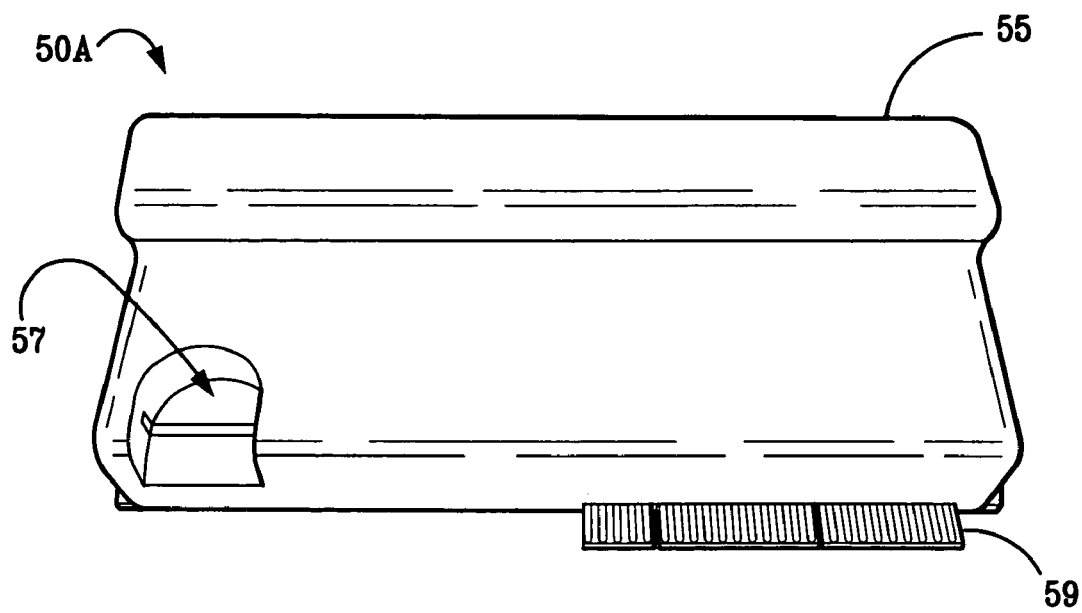
FIGS. 3A and 3B depict an exemplary embodiment of a disposable cartridge in accordance with the present invention.
Figure 3B:
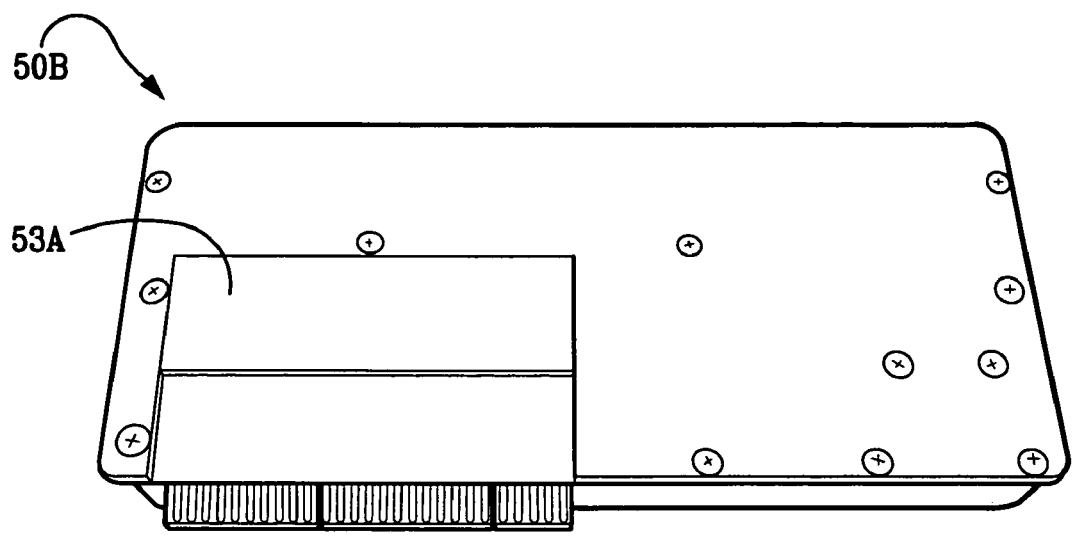
Figure 5:
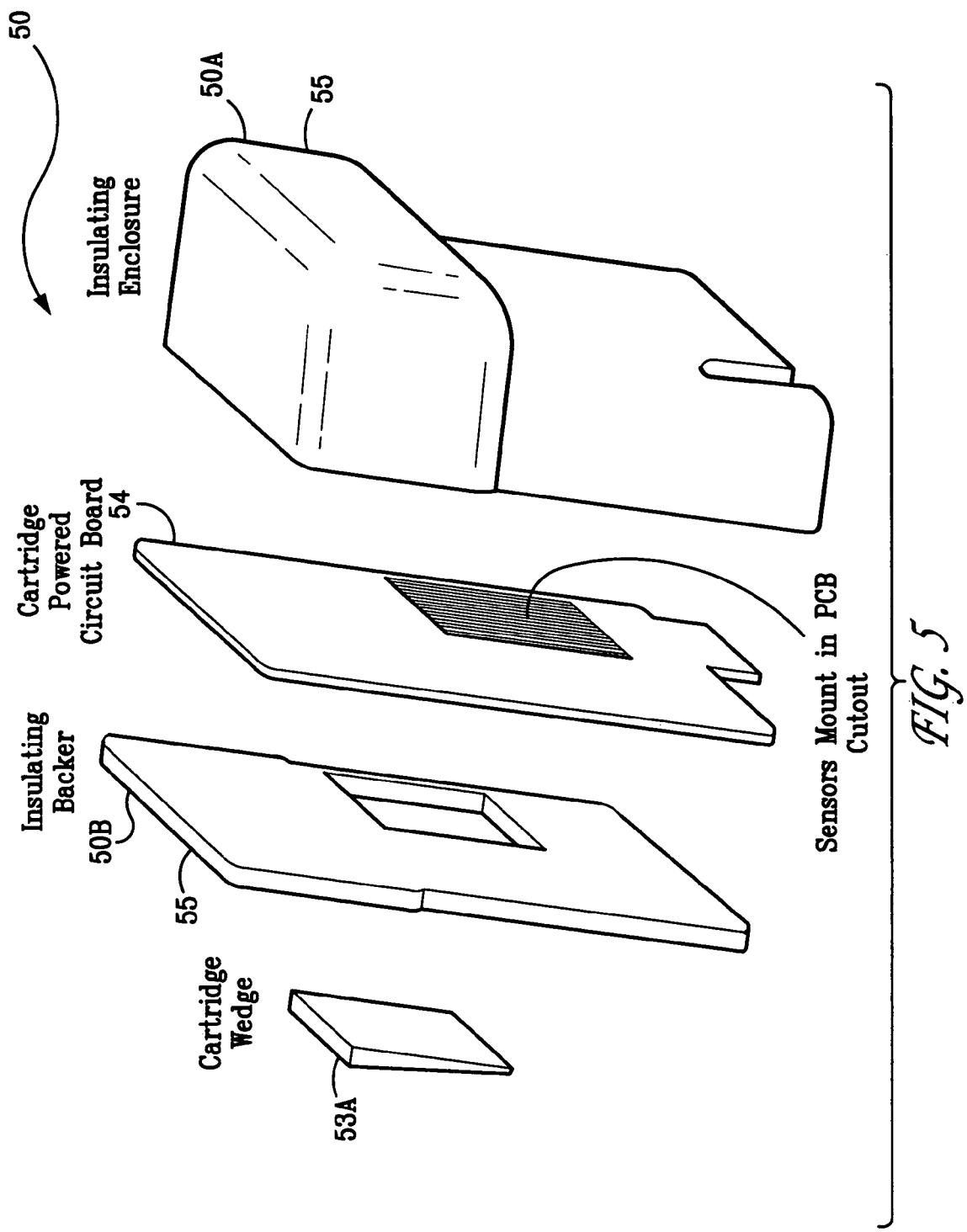
FIG. 5 depicts elements of the cartridge internals.

FIGS. 3A and 3B depict an exemplary embodiment of the disposable cartridge 50. The cartridge comprises a cartridge housing having front and back sides 50A and 50B; a sample injection port 41 (FIG. 1A); a plurality of SPR sensors 31 contained within the cartridge housing (see FIG. 4); and at least one battery (not shown) contained within the housing. The battery provides power for electrical components contained in the cartridge housing and the base unit housing when the cartridge housing is mated with the base unit housing. FIGS. 3A and 3B also show a wedge portion 53A, a thermally insulating plastic casing 55, which makes up the housing for the cartridge, a cutout 57 for mating with a peristaltic pump rotor contained within the base unit 10', and an electrical connector 59.

As shown in FIG. 4, the wedge portion 53A is part of a mating means 53 for mating a heat sink 60 with a base unit heater cooler 34. The mating means 53 also includes a wedge portion 53B for the base unit.

FIGS. 5, 6, 8, 9A-B, 10 and 11 depict various elements of the cartridge internals, including a printed circuit board 54, peristaltic tubing 56, a cut out 57A for mating peristaltic tubing with a peristaltic pump rotor 57B in the base unit, and a valve actuator 58.

The manner in which these elements may be constructed and arranged to provide a cartridge-based SPR sensing system in accordance with the present invention will now be described in greater detail 2. Hardware As mentioned above, in the exemplary embodiment (to which the present invention is by no means limited), each cartridge 50 contains the following components:

A. Eight (or in fact any number of) three-channel Spreeta 2000 SPR sensors;

B. Batteries providing power for the sensors and the base unit;

C. Heat sinking which serves to (1) equilibrate the sensors at a constant temperature; (2) equilibrate fluid stream to constant temperature; and (3) mate with TE heater/cooler in base unit (see FIG. 4);

D. Printed-circuit board which provides the physical frame for cartridge and electrical connections to batteries, sensors and other support electronics;

E. Thermally insulating plastic casing forming the front and back surfaces of the cartridge (exclusive of heat sinking regions) (see FIGS. 3A, 3B); and F. Sensor fluidics.

Figure 6:
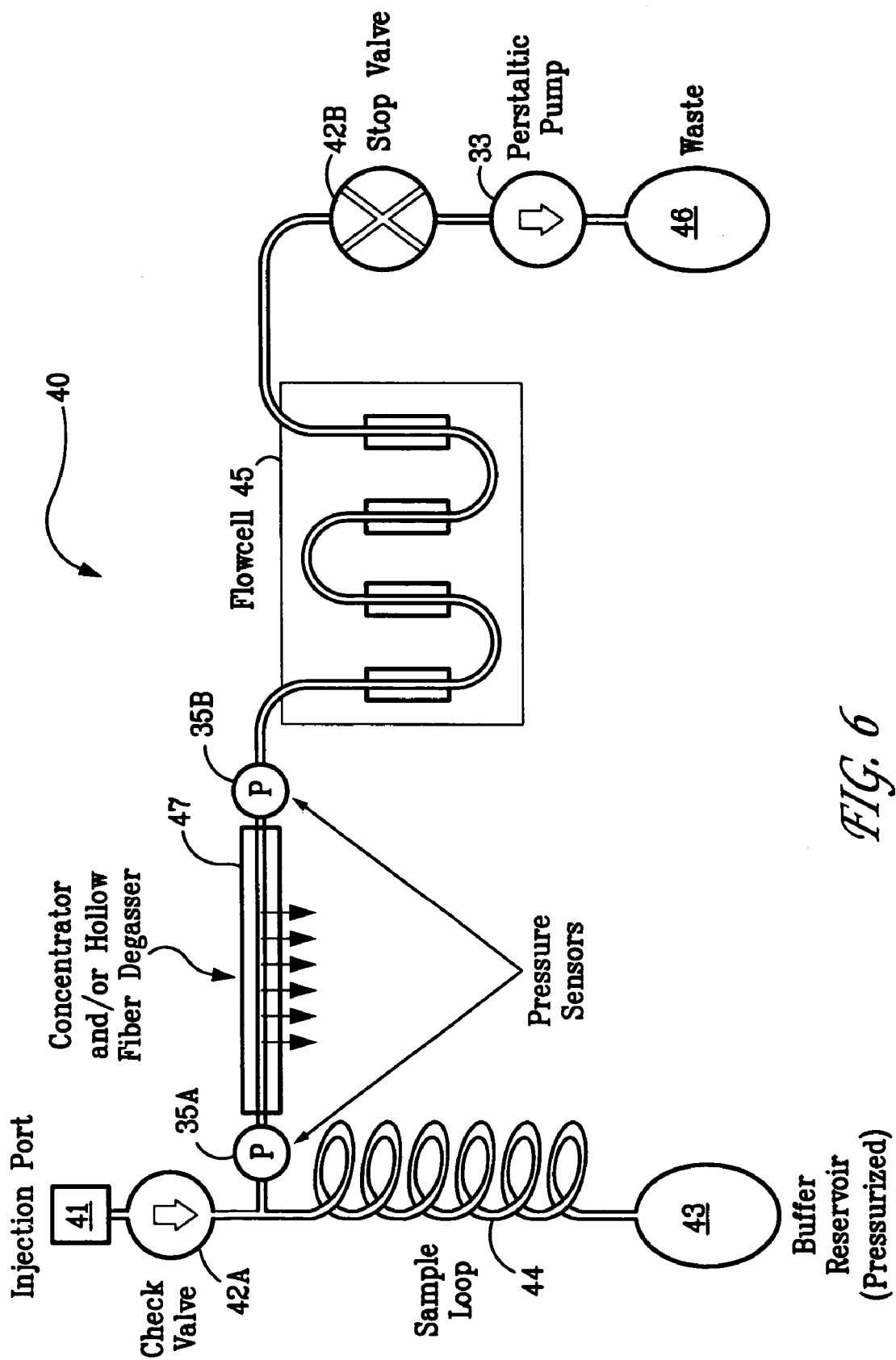
FIG. 6 schematically illustrates a fluidic system in accordance with the present invention.
Figure 7A:
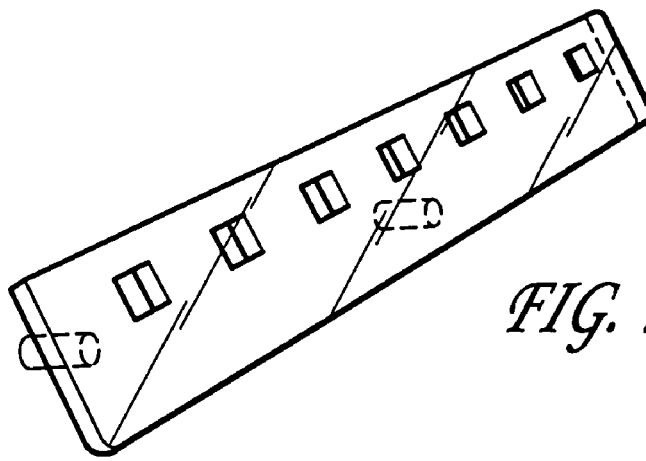
FIGS. 7A, 7B and 7C depict aluminum front and back plates of a flowcell, which serve to align the flowcell with sensors and equilibrate the temperature of flowing liquid.
Figure 7B:
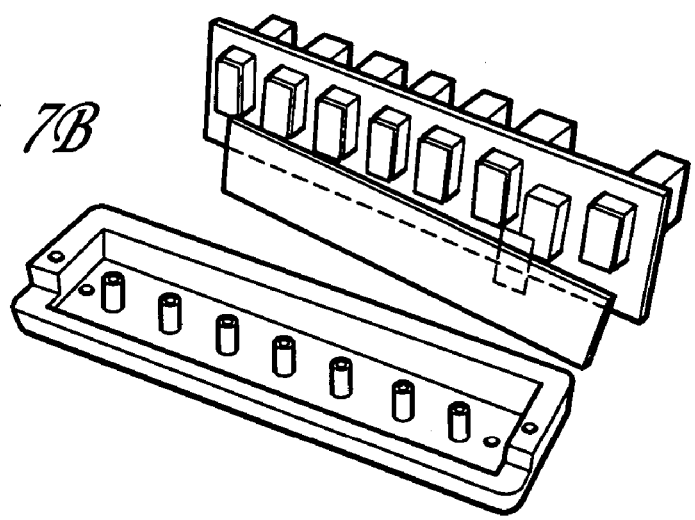
Figure 7C:
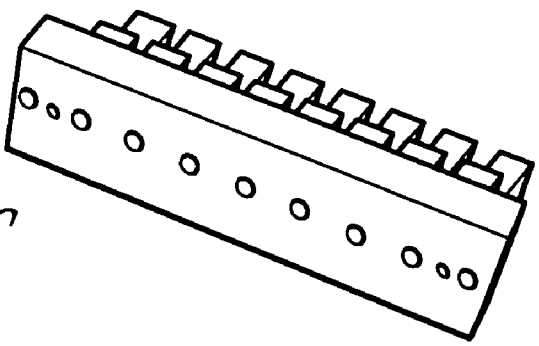

The sensor fluidics serve to (1) enable the user to inject a sample contained in a syringe into the cartridge; (2) perform simple preconditioning on the sample (concentration and/or degassing and temperature equilibration) and (3) flow the injected sample over the SPR sensor surfaces at a controlled rate. A schematic of the fluidic system is shown in FIG. 6. As shown, the fluidic system includes the following components:

1) A silicone molded flowcell 45 that provides a single flow channel covering all sensors in series. In addition to the silicone channels, the flowcell has aluminum front and back plates (FIGS. 7A-7C), which serve to align the flowcell to the sensors and equilibrate the temperature of flowing liquid.

2) A sample injection port 41 with check valve 42A;

3) A sample loop 44 with pressurized buffer reservoir 43;

4) A waste reservoir 46 that collects liquid at the end of the flow path, and a stop valve 42B;

5) Flow metering fluidics including silicone peristaltic tubing 56 with appropriate mounting and valves, designed to mate with a peristaltic pump rotor in the base.

Figure 8:
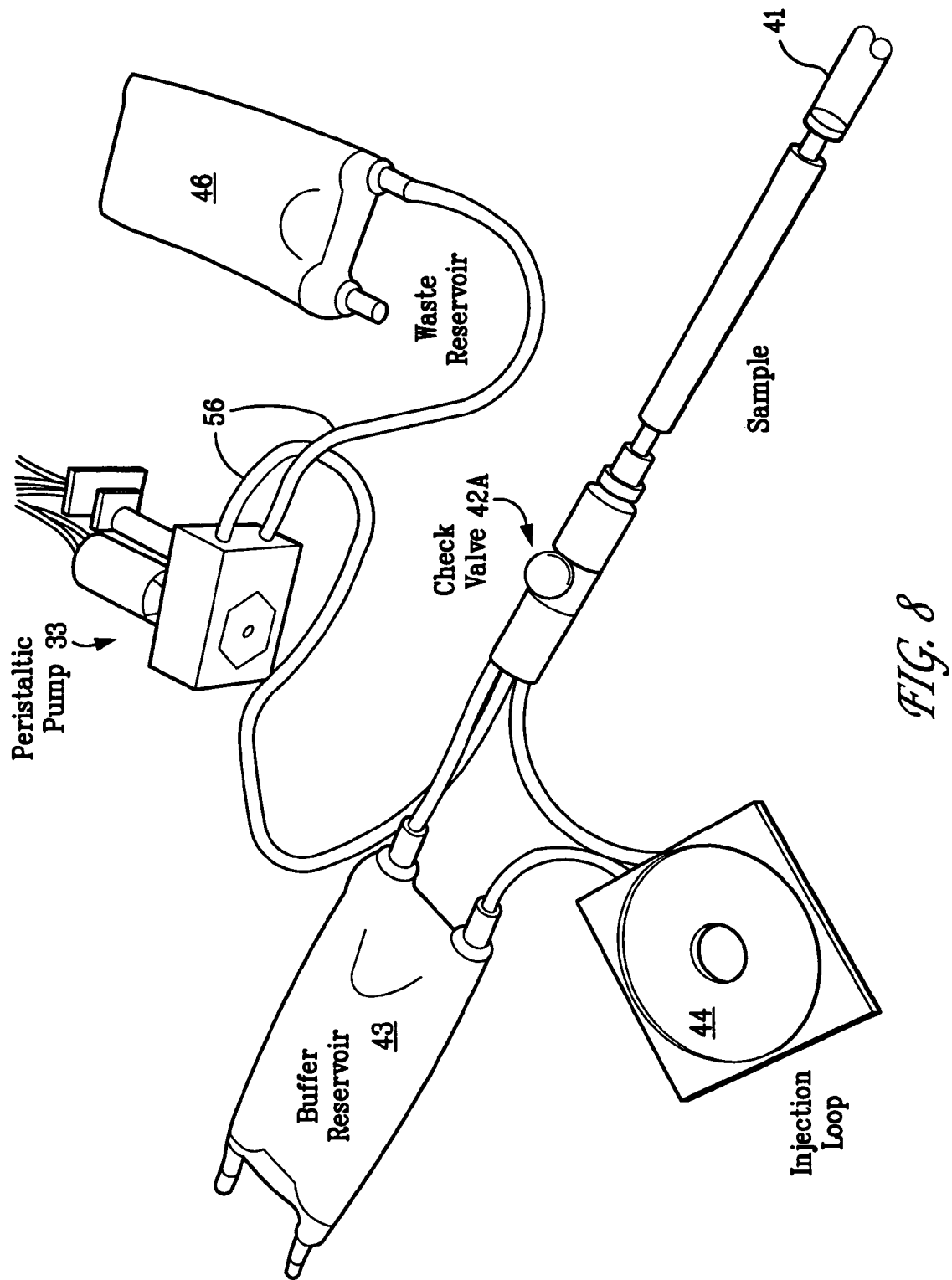
FIG. 8 depicts elements of a flow injection system in accordance with the present invention.
Figure 9A:
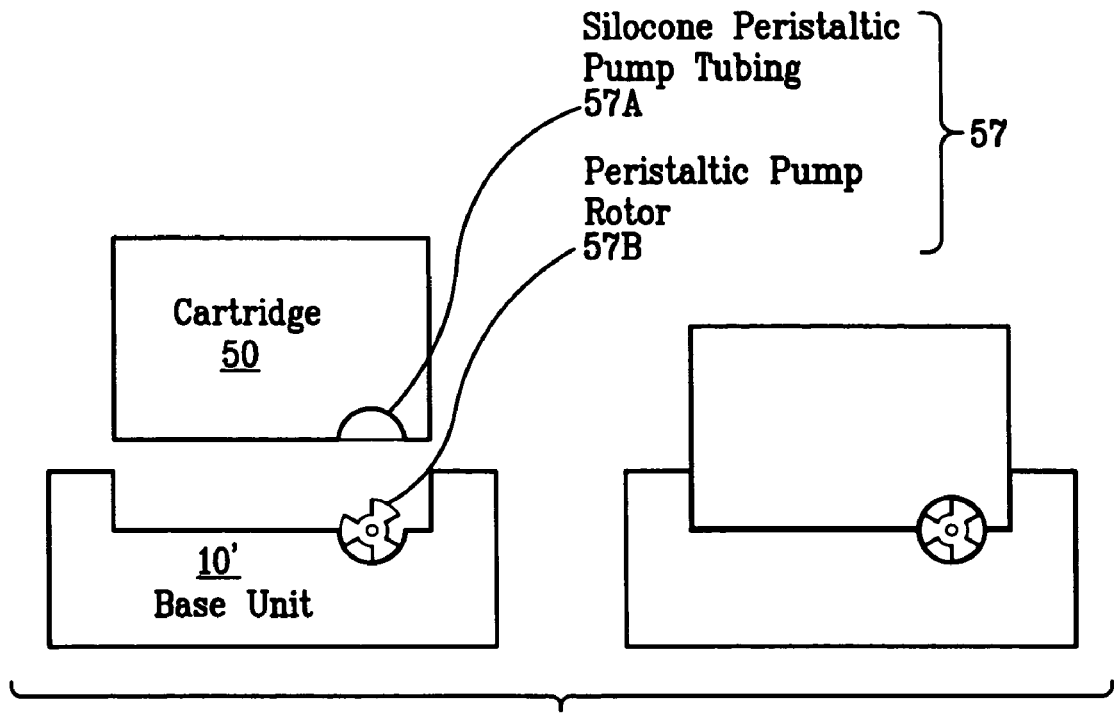
FIGS. 9A and 9B depict elements of a cartridge and base unit in accordance with the present invention.
Figure 9B:
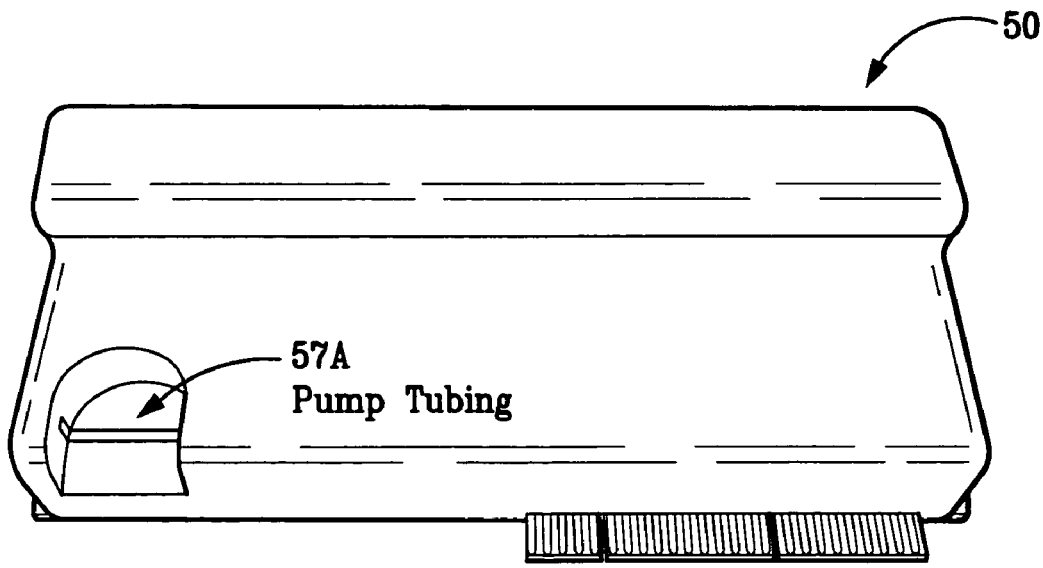

Together, these items (1-5) form a flow injection system, as shown in FIG. 8. The peristaltic pump meters the flow of buffer as it travels from the reservoir, through the injection loop, through the peristaltic pump, and into the waste reservoir. (As shown in FIG. 6, the complete system also includes pressure sensors 35A and 35B, an in-line hollow-fiber concentrator and/or degasser 47, flowcell 45, and stop valve 42B between the injection loop and the peristaltic pump. These are described further below.) When the user injects a sample via the injection port 41 into the check valve 42A, the sample displaces buffer in the injection loop, forcing buffer back into the reservoir. The sample then flows out of the injection loop and through the sensor flowcell 45 at the rate set by the peristaltic pump 33.

As discussed above, the flow system's peristaltic pump is composed of components in both the cartridge 50 and the base unit 10'. The pump tubing carrying the liquid sample is fully contained within in the cartridge, while the rotor which presses on the tubing and meters flow is contained in the base. When the cartridge is mated to the base unit (FIG. 9), the two components meet to form the complete pump unit. This division allows the liquid sample to be completely contained within the disposable cartridge while keeping the expensive pump rotor and motor in the base unit.

Figure 10:
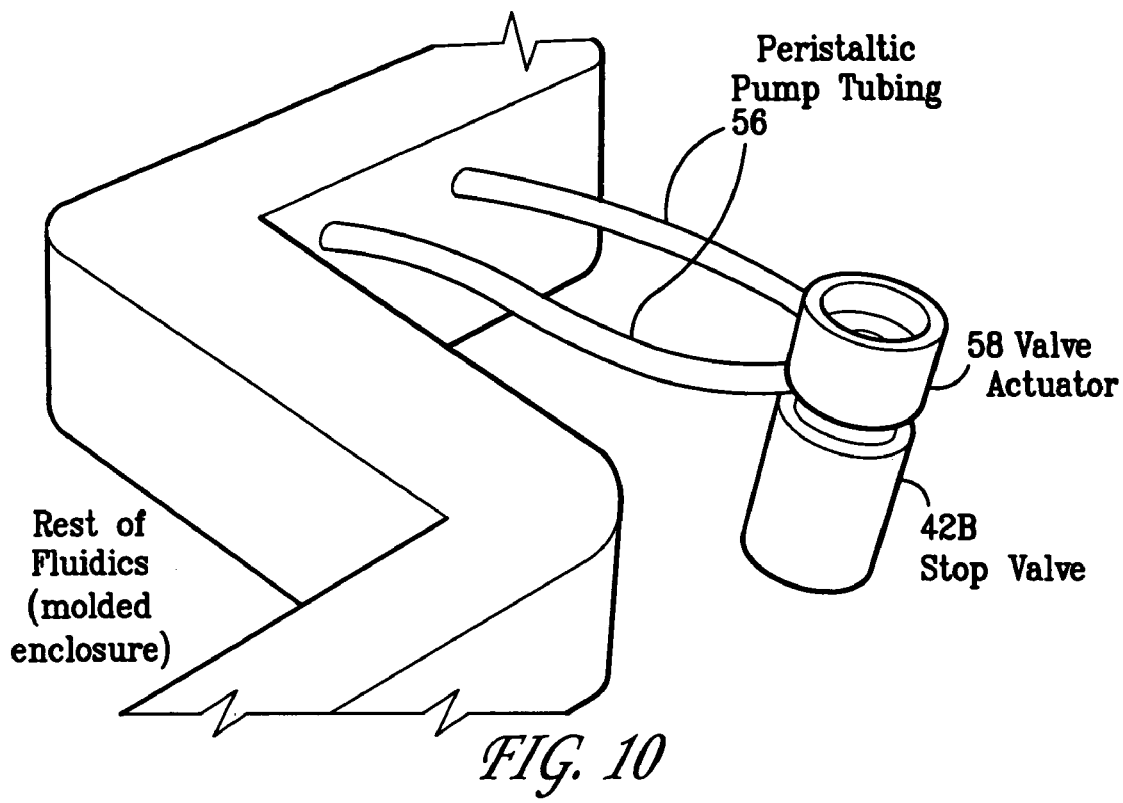
FIG. 10 depicts the coupling of a stop valve in the fluid path prior to peristaltic pump tubing.
Figure 11:
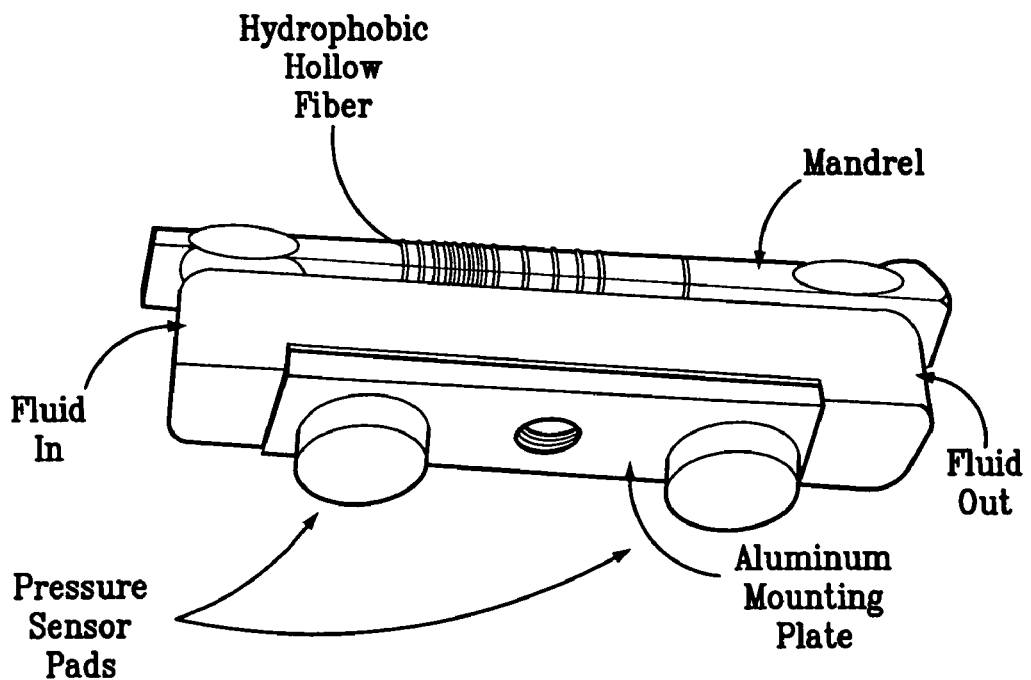
FIG. 11 depicts how pressure sensors may be mounted to monitor pressure difference across the degasser.
Figure 12:
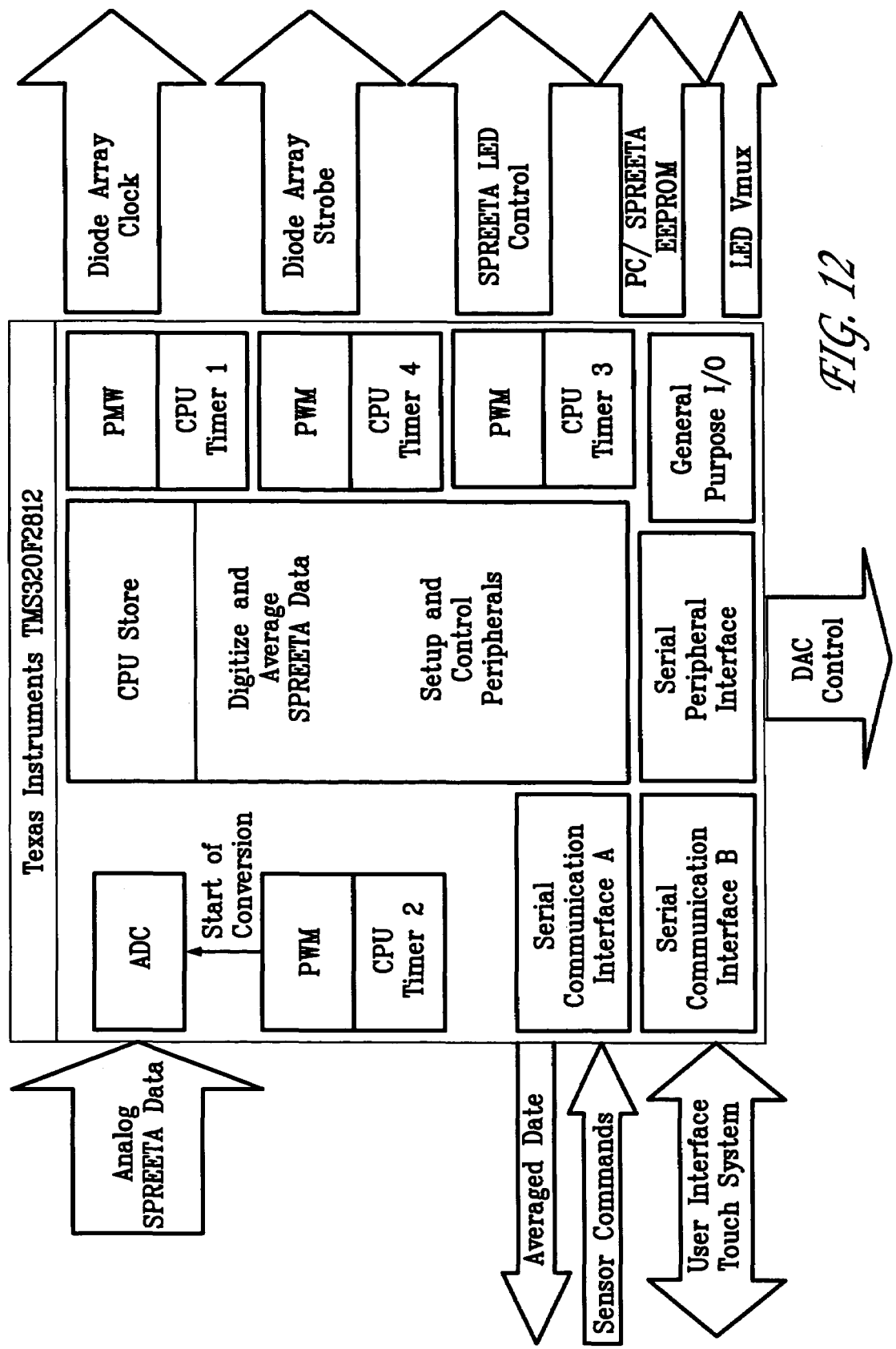
FIG. 12 schematically depicts certain reusable components of a base unit, including a digital signal processor, data acquisition and timing systems, etc.

In addition to items 1-5 enumerated above, the illustrative embodiment of the cartridge-based system includes the following:

6) An externally actuated mechanical valve that prevents fluid flow while the cartridge 50 is not engaged in the base unit 10'. In the flow system described above, flow is metered by the peristaltic pump formed by the combination of tubing contained in the cartridge and a pump rotor 57B contained in the base. When the cartridge is not in the base unit, the rotor is not present, and some other mechanism must be provided to inhibit flow. For this purpose, a stop valve 42B is placed in the fluid path just prior to the pump tubing 56, as shown in FIG. 10. The valve 42B is contained in the cartridge (not shown) and is normally closed (pinching the tubing under spring pressure). When the cartridge is inserted into the base unit 10', a lever is engaged to extend a plunger through a hole in the front of the cartridge and up against the valve actuator 58, allowing liquid to flow and also latching the cartridge into the correct position relative to the pump rotor 57B.

Figure 14:
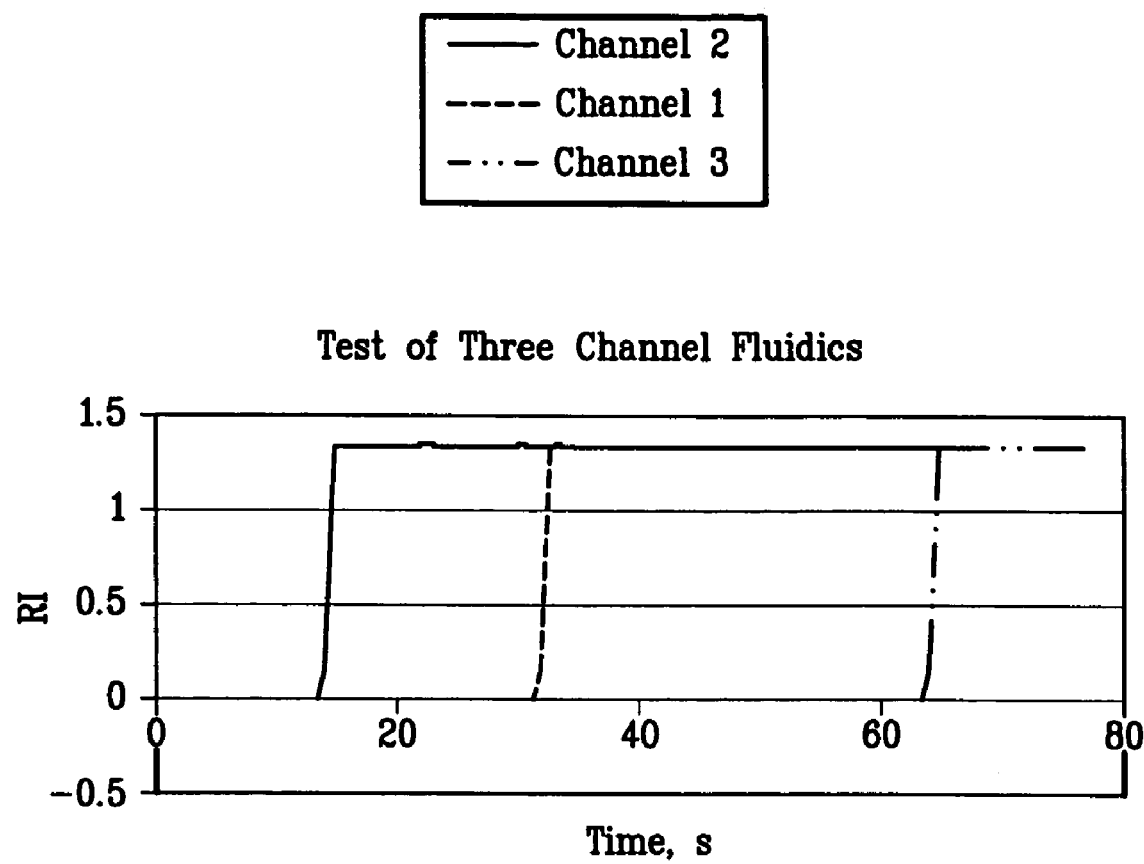
FIG. 14 illustrates exemplary waveforms demonstrating the separate channels of a three-channel sensor reacting to the injection of liquid.

7) A hollow-fiber concentrator and/or degasser 47 (see FIGS. 6 and 14). To eliminate the possibility of distortion of SPR measurements by bubbles in the sample stream, a concentrating and/or degassing apparatus is placed in the fluid path prior to the sensor flowcell 45. This device routes the sample stream through a single 6" long, 200 μm ID gas-permeable hollow fiber. Because the sample stream is under pressure relative to ambient pressure, bubbles and dissolved gases will tend to exit through the walls of the fiber, while liquid cannot pass through the pores in the hydrophobic fiber walls. Similarly, hollow fiber concentration uses small tubes with special walls that are porous to salt water but not to larger proteins. Thus, a hydrophilic hollow fiber concentrator of appropriate cutoff dimensions may be employed as a concentrator. Small surface-mount pressure sensors 35A, 35B (FIG. 6 and FIG. 11) mount to pads at both ends of the fiber, and serve to (a) monitor the pressure in the system, enabling detection of leaks and clogs; (b) monitor the presence of air bubbles in the sample stream; and (c) by measuring the pressure drop across the fiber, provide an independent measurement of system flow rate.

The cartridge may be built so that sensors, batteries, buffer, etc., can be replaced easily, or preferably the cartridge will be designed such that the entire cartridge is a self-contained, maintenance-free disposable unit containing reagents and battery power sufficient for performing a large number of sensing cycles (target of 30+).

The cartridge 50 mates with the base unit 10', which contains components of the sensor system intended to be reused. These include the following:

1) Mechanical, electrical, and thermal interfaces for mating with cartridges;
2) Custom electronics for driving the Spreeta sensors, conditioning the sensor outputs, providing interfaces for auxiliary measurements and sensor functions such as temperature control and read/write of the sensors' embedded memory chips, and providing interfaces between sensor components and between sensor components and external devices;
3) Digital signal processor (DSP) single-board computer (COTS, TMS320F2812 based) with integrated 16-channel, 12-bit ADC for data acquisition, accumulation of sensor spectra, generation of instrument timing, communication with internal instrument peripherals, delivery of data to and reception of commands from external devices (FIG. 12);
4) Web-based graphical LCD touchscreen interface for implementation of self-contained user interfaces and prototyping of alternate hardware user interfaces;
5) TE heater/coolers with efficient drive electronics, heat sinking, and provision for mating to cartridge thermal surfaces and regulating sensor temperature under DSP control. Drive electronics are designed for low power operation.
6) Computer-controlled motor-driven peristaltic pump rotor configured to mate with silicone cartridge fluidics for flow metering;
7) Connectors to external devices (e.g. for data download);
8) Rugged thermoplastic case (Pelican) containing the base unit and cartridge.

3. Software

Low-level instrument functions may be performed by the instrument's embedded DSP, programmed in "C" using Texas Instruments° Code Composer Studio. The DSP has processing power sufficient to perform high level functions (data analysis, user interface control); however, these need not be implemented in the DSP but rather low level data may be sent to a PC over an RS-232 serial port for further analysis. Low level software functions include the following:

1) Generation of timing signals needed for driving the Spreeta sensors;
2) Digitization and accumulation (summing) of Spreeta sensor spectra for each of 24 sensor channels;
3) Delivery of accumulated spectra over serial port at periodic intervals (~1 s);
4) PID control of sensor temperature via TE heater/cooler hardware;
5) Interpretation of incoming serial port commands (e.g., for setting of LED levels, integration times, pump speed); and
6) Control of other components of sensor hardware via SPI interface.

3. Techniques for Production and Application of Silicone Molded Flowcells

Liquid surface functionalization of separate channels of an SPR biosensor with multiple channels spaced as small as 200 microns apart can be accomplished through precise registry of the separate channels. Silicone is a good candidate for this because it can create a liquid seal with very little surface contact and can be molded with a precisely machined mold. When using a silicone molded flowcell, however, the contact pressure with the surface should be tightly regulated to avoid over or under compression and subsequent loss of flow. Both lateral registry and precise compression can be accomplished using a three-part system comprising molded silicone, a rigid plate holding the sensor, and a cover plate.

The Mold

Design and construction: Precise registry and separation of the flow channels of the PDMS mold may require precision machining.

Casting with tapered nylon line: Tapered nylon line can be purchased in many different sizes and is an ideal candidate for creating flow channels in molded silicone. The tapered line may be inserted into a hole drilled in the mold, and then pulled through until it is tight, thus creating a tight seal that no liquid silicone can leak into. This method is best for straight channels.

Silicone cast of mold: Liquid silicone may then be poured into the mold, and a cover placed over the top. After the silicone cures, the nylon line can be pulled out, and the silicone cast can be easily removed from the mold.

Casting silicone tubes into the PDMS mold: Routing flow channels through a complex flow system can be challenging. Casting silicone tubes into the silicone mold allows for the creation of more complex flow arrangements. Tapered nylon line can be threaded through the silicone tubes, and a connection to the flow cell chamber can be made as described above.

Front and Back Plate

Figure 13B:
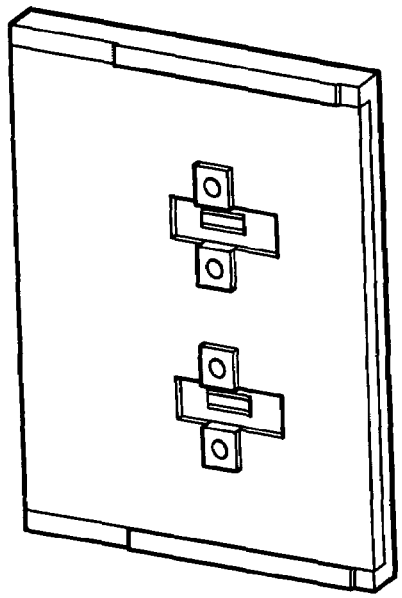
FIGS. 13A, 13B, 13C and 13D depict front and back plates and the mounting of a flowcell and sensors.
Figure 13D:
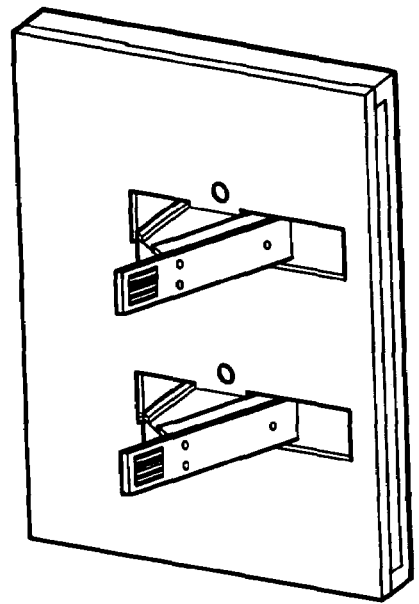
Figure 13A:
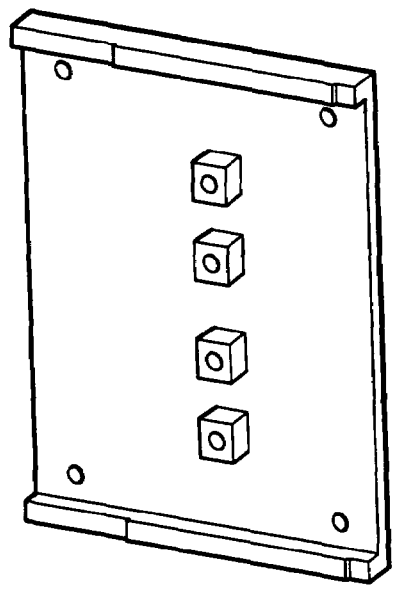
Figure 13C:
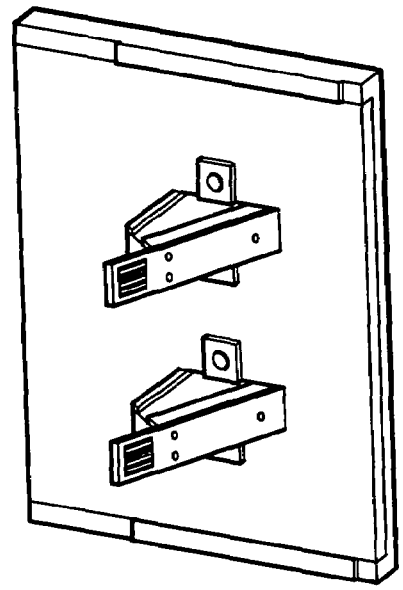

Registry of lateral and height dimensions using the cover plate: Registry of both lateral and height (compression) dimensions can be accomplished using a rectangular post machined in the cover plate on either side of the sensor. The height of the post determines the amount of compression of the silicone layer, while the location of the posts on either side of the sensor aligns the sensor with the PDMS flow cell. See FIGS. 13A-13D. FIG. 13A depicts the cover plate with registry posts. FIG. 13B depicts the cover plate with a PDMS flow cell inserted. FIG. 13C depicts sensors aligned with the flow channels between posts. FIG. 13D depicts how the back plate compresses the registry posts to precisely regulate compression of the silicone, holding the sensors in place vertically.

SPR Data

FIG. 14 demonstrates the separate channels of a three-channel sensor reacting to the injection of liquid. As the liquid is introduced, the sensing area goes from air (RI=0) to water (RI=1.333). At time T=15 seconds liquid was injected into channel 1, at time T=30 seconds liquid was injected into channel 2, and at time T=60 seconds liquid was injected into channel 3. This demonstrates the segregation of liquid flow within the flow system.

C. Portable SPR Sensing System

1. Introduction

Figure 15:
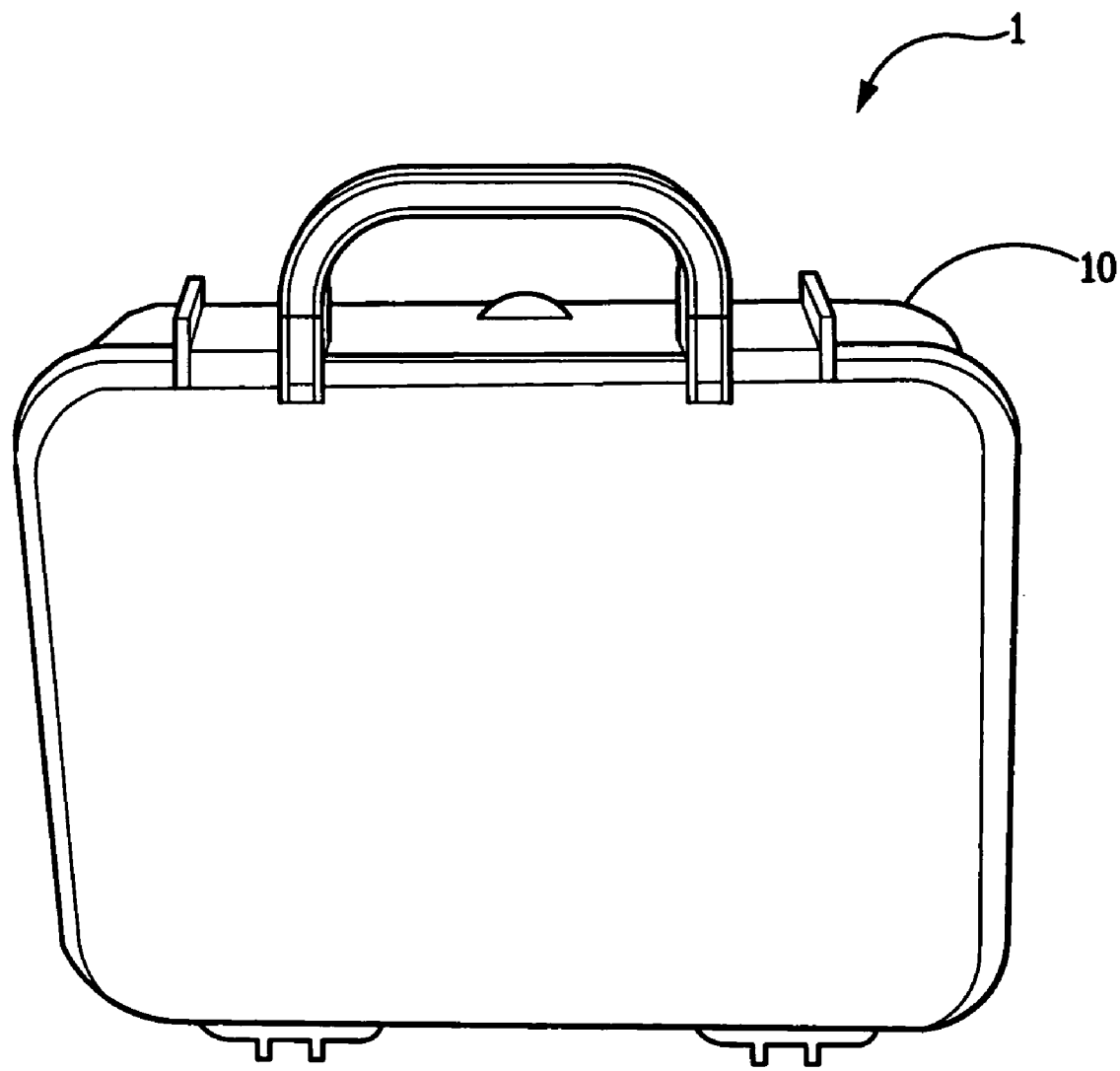
FIG. 15 illustrates the outer housing of a portable SPR sensing system in accordance with a second embodiment of the present invention.

The portable (non-cartridge-based) instrument may likewise be used to detect the presence of biological and chemical agents in a fluid. This embodiment is designed for laboratory use and the current, exemplary model utilizes two 3-channel sensors in a positive pressure semi-automated sample injection system. As shown in FIG. 15, the device is hand portable and enclosed in a durable watertight case. A personal computer using Texas Instruments SPReeta software interprets data fed through a serial port for each sensor. The system is then capable of detecting small changes in mass at the surface of the sensor. Antigen-antibody interactions as well as other specific intermolecular interactions can be detected using these sensors.

2. Electrical System

The major electrical sub-components of the exemplary system include the following, although it should be noted that the invention is by no means limited to these specific components, as will be readily understood by those skilled in the art of designing SPR instrumentation::

1) Texas Instruments Digital Signal Processors (SPRDSP-005v113)
2) Texas Instruments SPREETA Sensor (TISPR2K23)
3) Wavelength Electronics Temperature Controller (HTC-3000)
4) Instech Miniature Peristaltic Pump (P625/900.143)
5) Gast Miniature air pump (5D1060-101-1030)
6) Red Lion Miniature Voltmeter (MDMV)
7) Lee Valves 3-way Valve (LFYAI216032H).

2.1 Design and Function

1) The TI DSPs are only altered to replace the conductors used for power. The DSPs interface with the sensors and provide serial output to a PC.

2) The HTC-3000 is mounted to the back of the panel and thermal paste is used to promote heat dissipation. A custom designed board interfaces with the controller and allows use of connectors. The temperature is set using a ten-turn potentiometer and monitored using a miniature voltmeter with LCD display.

3) The system flow rate is controlled using a miniature peristaltic pump placed downstream of the flow cell. The pump speed is varied using a ten-turn potentiometer.

4) Air pressure from a Gast air pump is used to drive fluids through the system at approximately 10 psig. The positive pressure is applied at the buffer reservoir and is not specifically controlled.

5) The system flow is directed using three Lee 3-way valves. Relays in line with "flush" and "inject" switches turn off the peristaltic pump during the specified functions.

6) Power is 12 VDC, supplied by an external or internal power supply.

Figure 16:
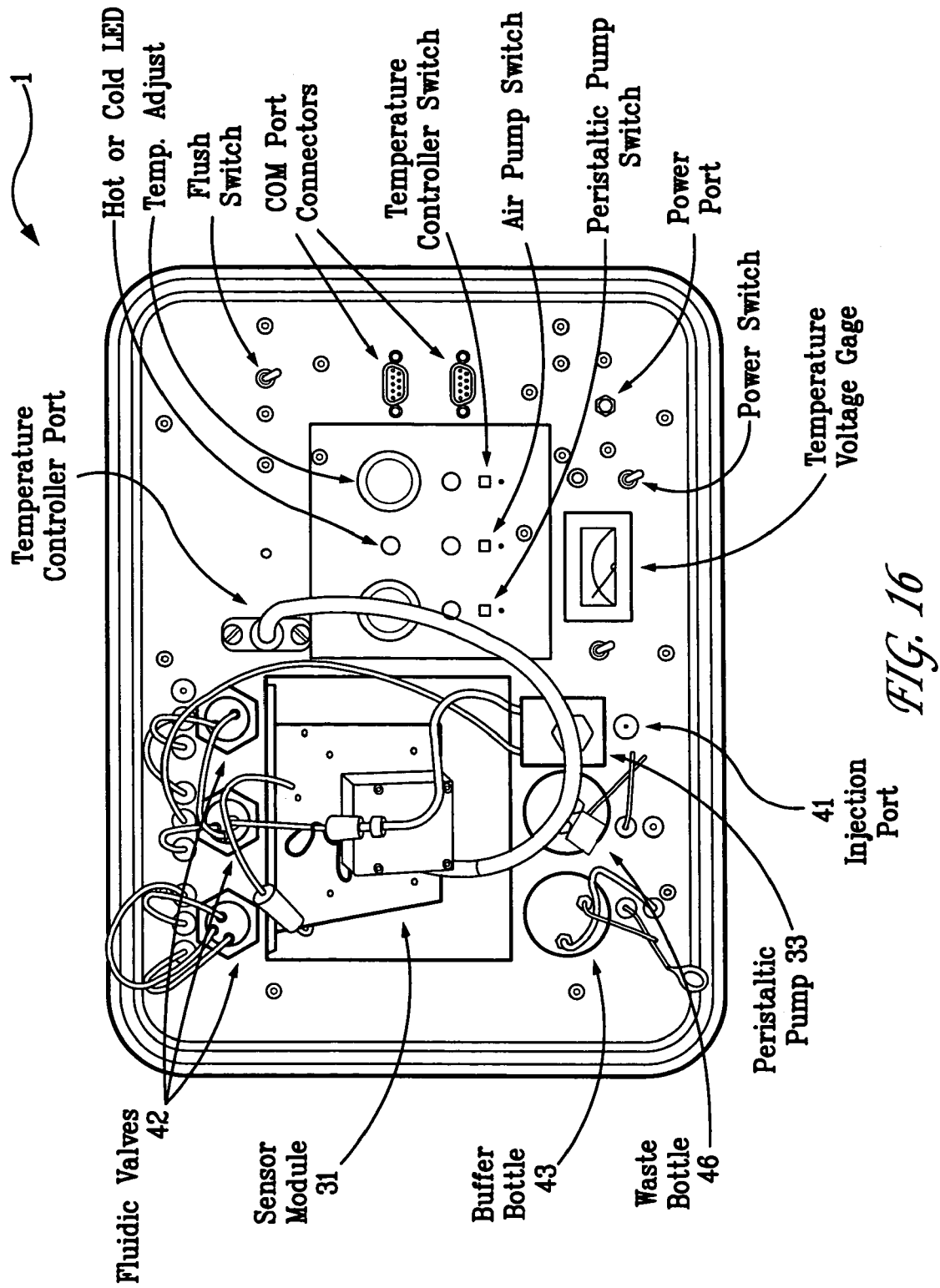
FIG. 16 illustrates an exemplary configuration of certain components of the portable SPR sensing system of FIG. 15.

These items are represented in FIG. 16.

2.2 Instrumentation Layout Changes From prior designs.

1) The system has been designed to reduce the exposure of electronic equipment to liquids used in SPR analysis.

2) A voltmeter has been integrated into the panel to eliminate the need for and external voltage measurement source.

3) Valves have been contained under the panel to reduce the complexity and opportunity for plumbing damage.

4) Flush and injection switches were added to the panel (functionality discussed below).

5) Power is now an external 12V source to reduce electrocution hazard.

6) A bi-color LED indicates heating or cooling of the sensor housing by the temperature controller and single color LEDs indicate activation of the adjacent switch.

3) System Fluidics

The system incorporates three 3-way valves with "zero" dead-volume, manufactured by the Lee Company. It is important that these valves be zero dead-volume to prevent the fluids trapped in unused legs from diffusing slowly into the current flow and affecting the SPR baseline. The sensitivity of SPR sensors to very small RI changes requires this zero dead volume fluidics. As indicated in the FIGS. 17-19, the valves are set to one of three conditions and FIG. 20 illustrates an automatic sample mode.

Figure 17:
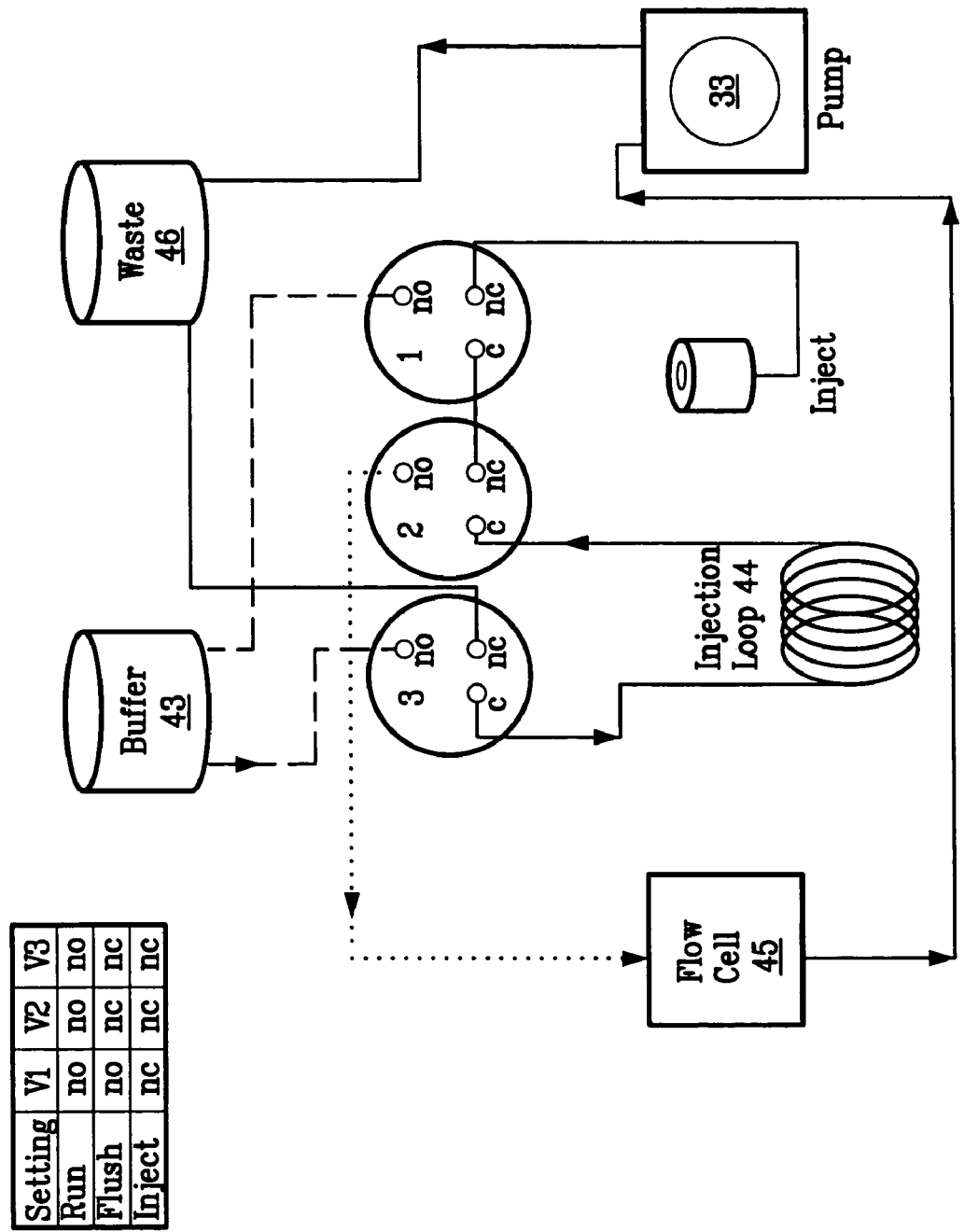
FIGS. 17, 18, 19 and 20 illustrate normal, injection, flush and auto sampler modes of operation of the portable SPR sensing system, respectively, in accordance with the present invention.

Normal flow mode is depicted in FIG. 17. In this condition, no power is applied to the valves and all valves are in their "normally open" condition. This provides a continuous flow from the pressurized buffer reservoir, through the injection loop, across the sensors, and to the vented waste container.

Figure 18:
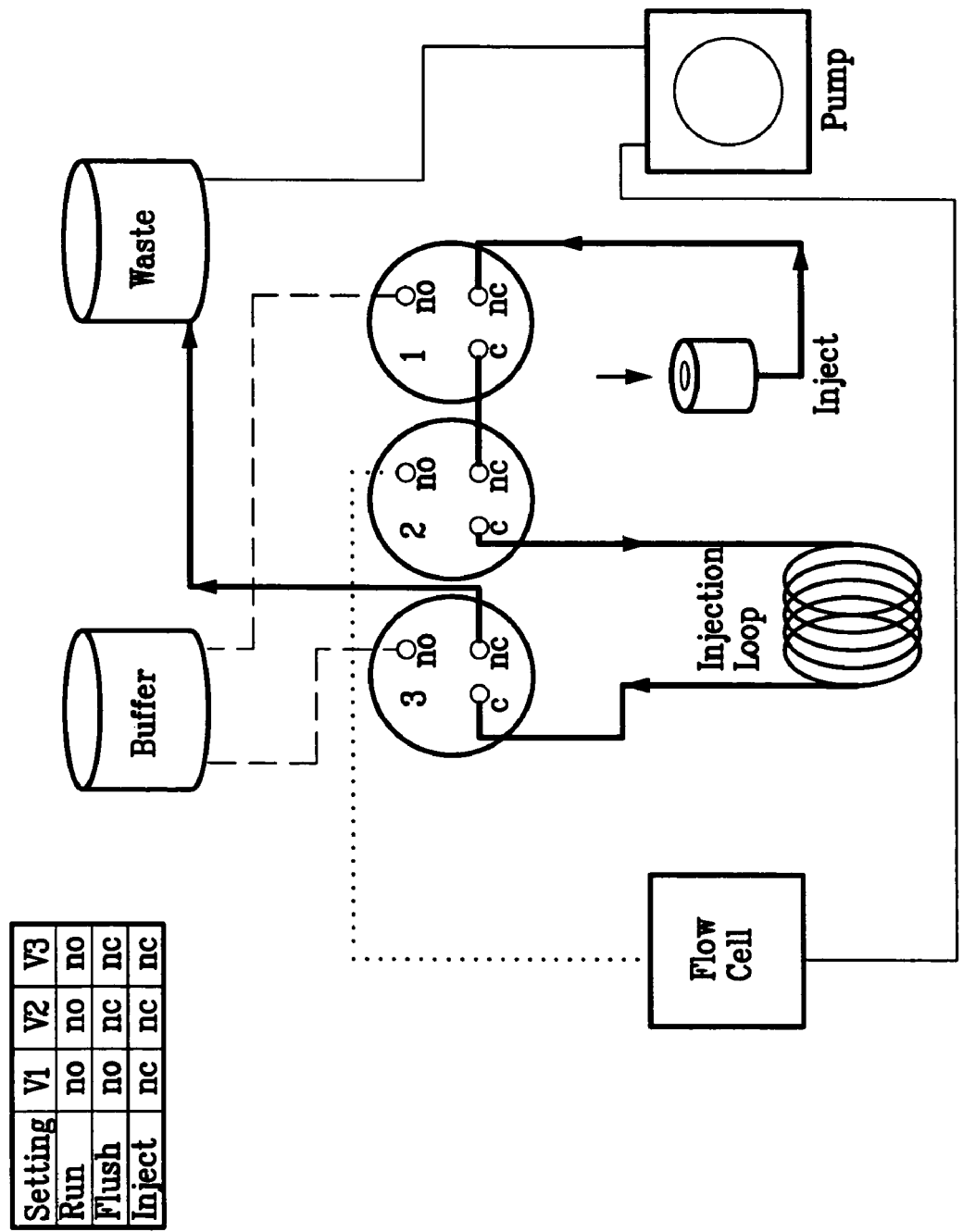

Injection mode is depicted in FIG. 18. During injection mode, a needle is placed in the injection port and the flow is routed through the injection loop and into the waste container. The peristaltic pump is disabled during this operation and 12VDC is applied to valve 2 and 3. Injection mode fills the injection loop with the sample fluid. Any fluid volume beyond that of the injection loop (including the swept volume of the valves in-line) is drained to waste. This allows for complete rinsing of the injection loop.

Figure 19:
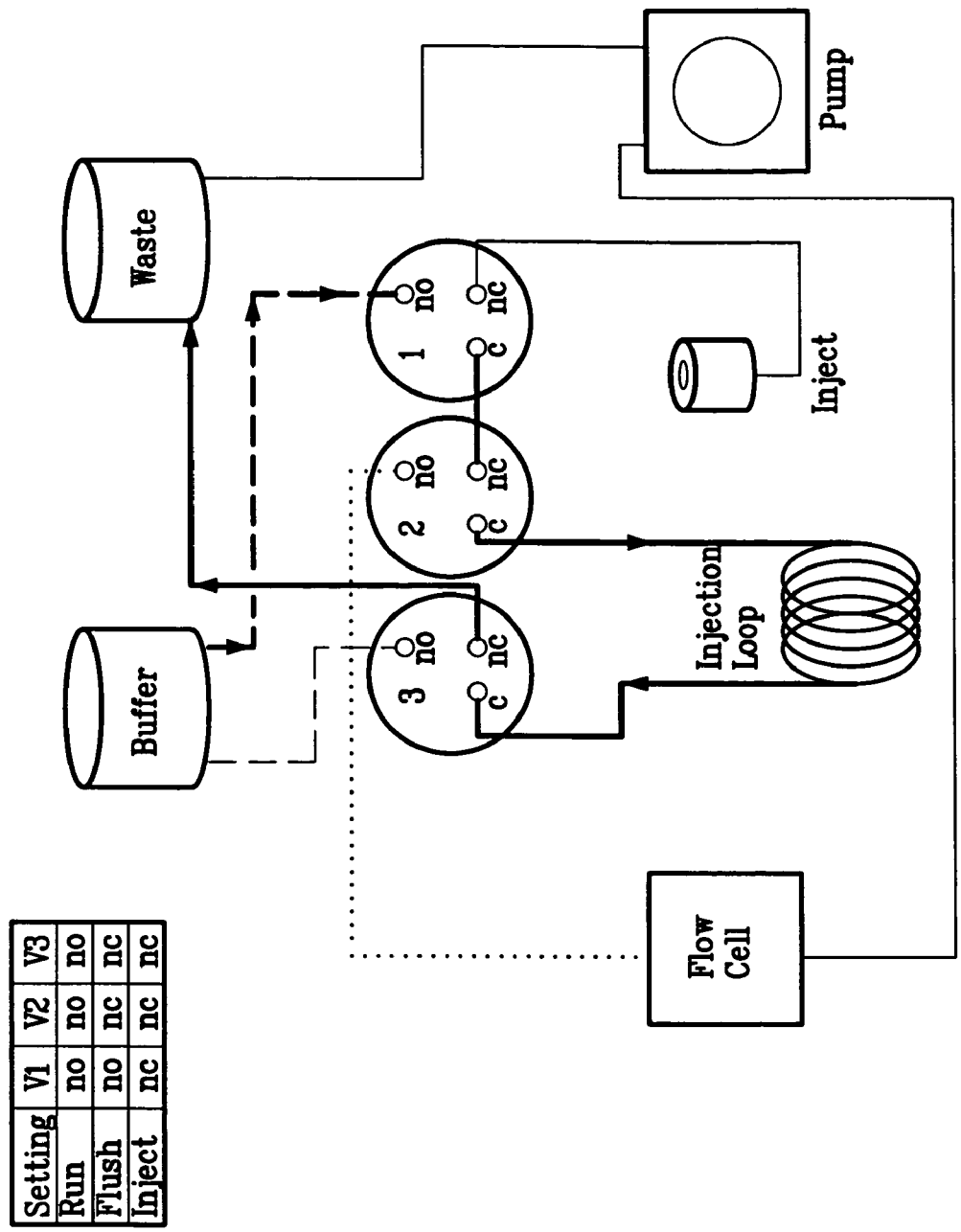
Figure 20:
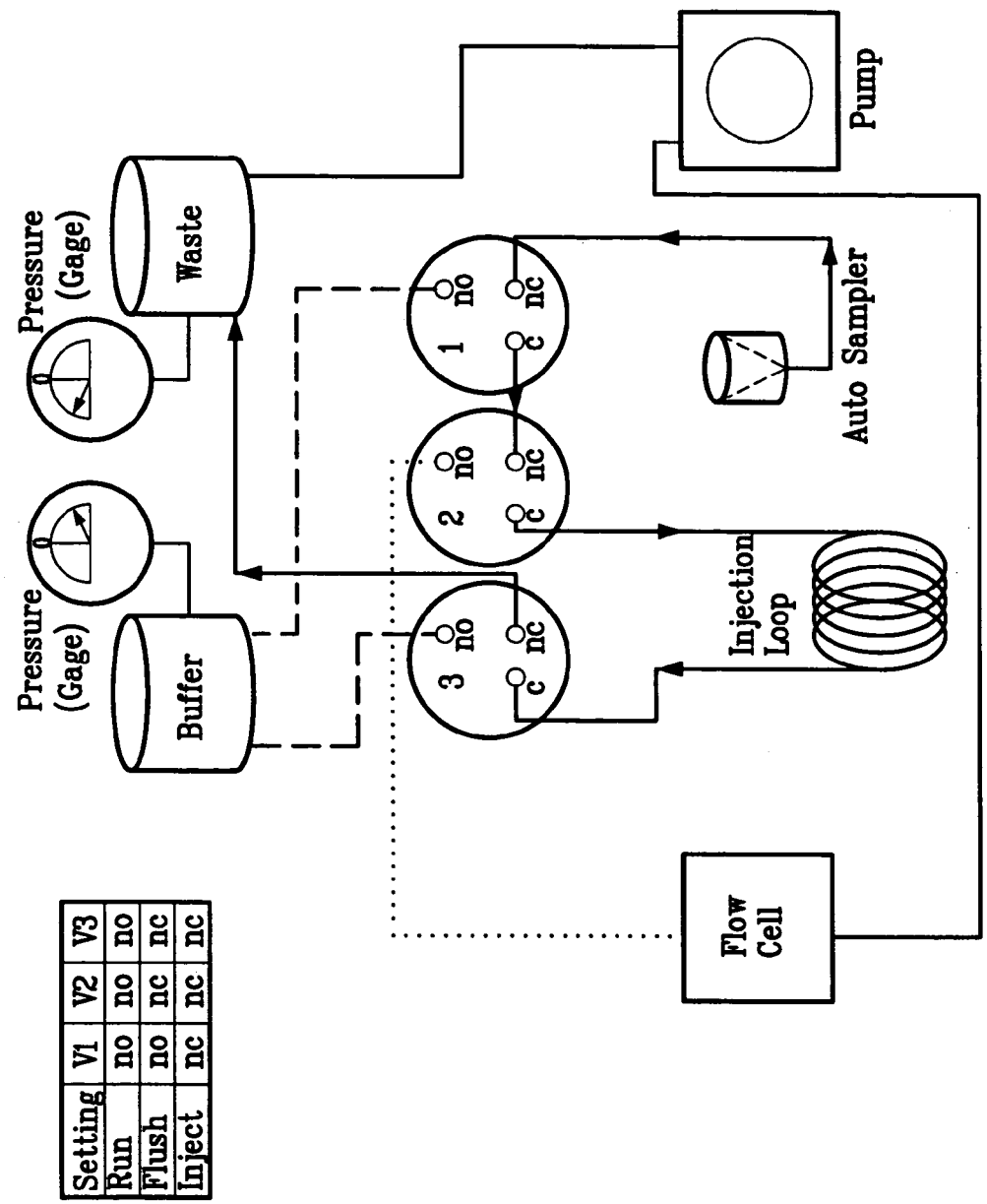

Flush mode is depicted in FIG. 19. Flush mode serves two purposes: (1) to clear any remaining injected fluid from the loop and replace it with buffer, and (2) to eliminate any diffusion between the buffer solution and the sample. This mode bypasses the peristaltic pump and runs the buffer through the loop and straight to the waste. Typically, this is at a high flow rate and cleans the system quickly.

Auto sampler mode is depicted in FIG. 20. In addition to a syringe injection system, an auto sampler has also been developed. A vacuum pump is used to create negative pressure on the waste container, which then draws the sample from a sample container, filling the injection loop. Liquid flow is the same as that of the "inject" flow schematic shown in FIG. 18. The automatic sampling system requires no syringe pressure to fill the loop, and thus can be incorporated into unattended sensors sampling from a liquid stream or particle collector.

Important system characteristics include the following:

1) Positive pressure. Experimentation has shown that the use of a positive pressure system with a peristaltic pump to meter the out flow results in far fewer bubble issues than with a peristaltic pump alone.

2) Dead volume. It is important that dead volume be minimized to avoid mixing of differing fluids trapped in the valve.

3) Critical volume. The volume after valve 2, leading to the flow cell, is critical. This volume divided by the flow rate is the time required for the sample fluid to reach the sensor. In addition, resulting tube length and volume contributes to wall effects resulting in diffusion of the liquids.

4) Sensor Housing

Temperature equilibration. In order for the sensors to work effectively, the sensor modules should be controlled to a precise temperature. Liquid introduced to the sensor should also be matched to the sensor temperature. The sensor housing assembly was designed to accomplish both of these objectives by encasing the sensors and the liquid input tubes in an insulated, temperature controlled aluminum housing. This design also makes the sensors modules replaceable with a minimum of effort.

Figure 21:
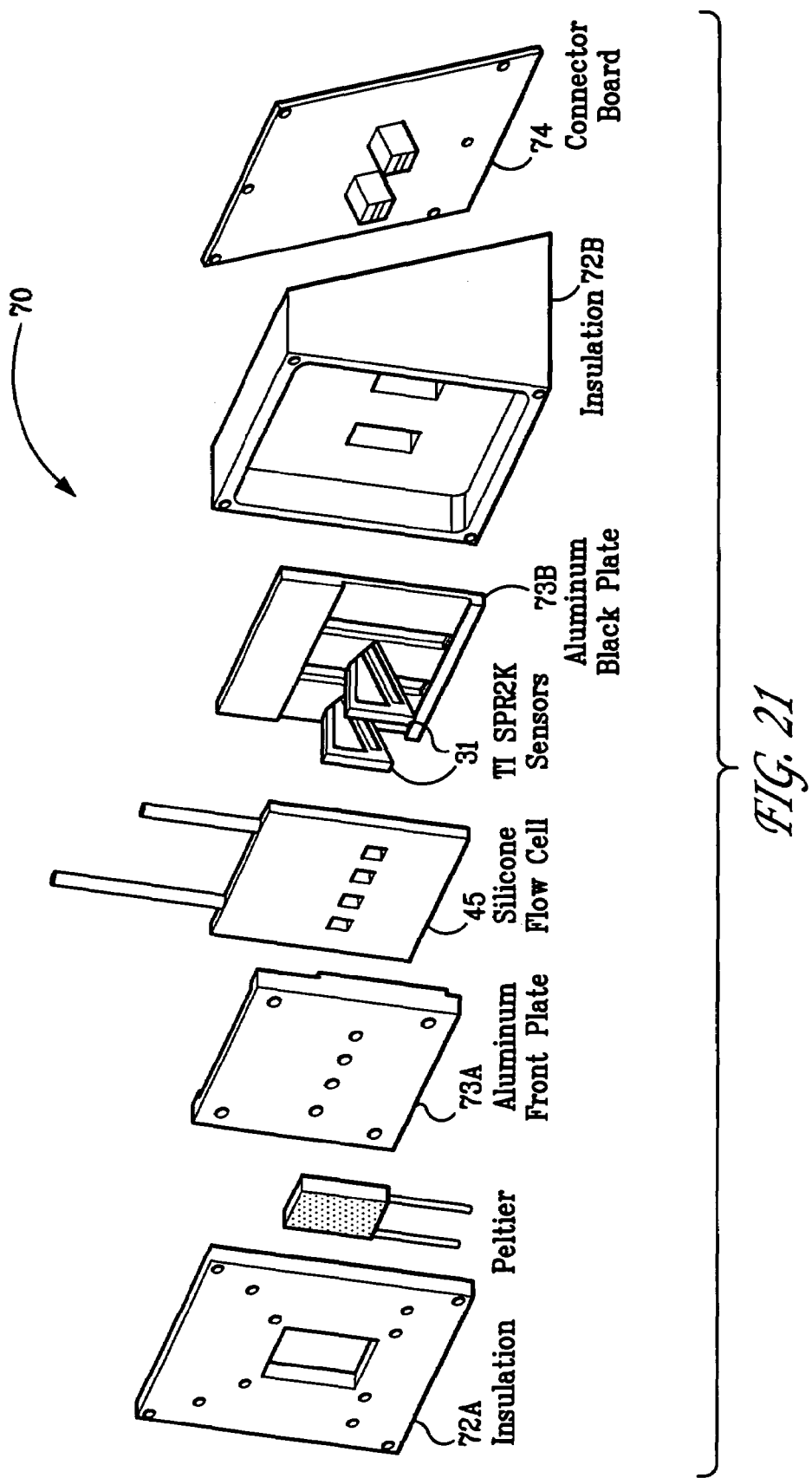
FIG. 21 depicts elements of an illustrative sensor housing.

FIG. 21 depicts the major elements of the sensor housing. These include a Peltier 71, front insulation 72A and back insulation 72B, front aluminum plate 73A and back aluminum plate 73B, and connector board 74. Also shown are the silicone flowcell 45 and SPR2K sensors 31. (The Peltier 71 may also be known as a Peltier Junction. It is well known that, when electrical current is applied to a thermocouple, a temperature difference is created, with one side of the thermocouple being hotter than room temperature and the other being cooler. A Peltier can be used to cool a device, where the cool side contacts the device and the hot side contacts a heat sink.)

Figure 22:
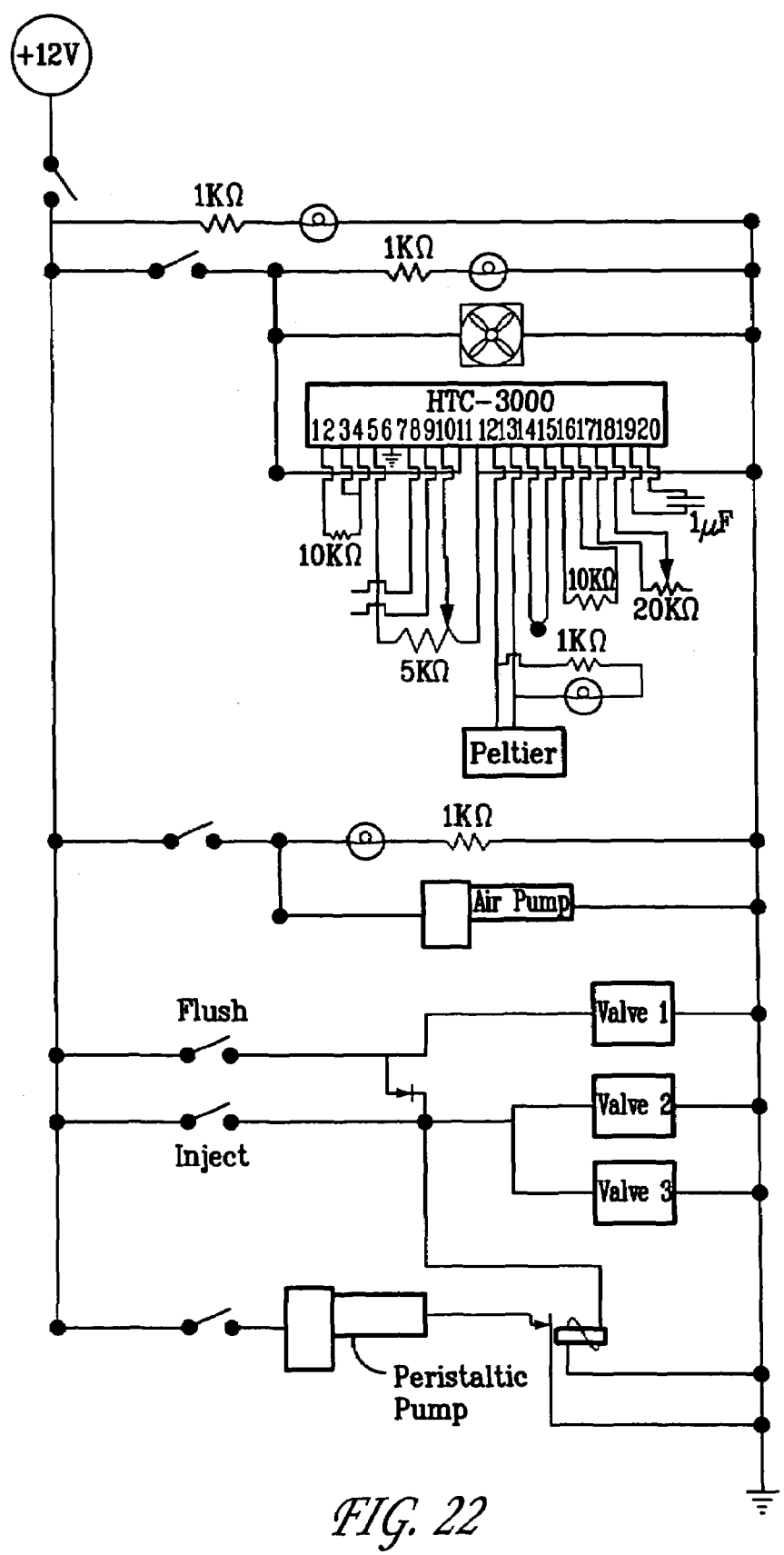
FIG. 22 is a schematic circuit diagram of the illustrative embodiment of the portable SPR sensing system of FIGS. 15-21.

FIG. 22 is a schematic circuit diagram for the illustrative embodiment of the portable SPR sensing system as described above.

D. Illustrative Protocols

We will now briefly discuss several protocols that may be used for detecting different types of target compounds or biological agents, etc. These include small organics, protein toxins, low concentration analytes, viruses, and the like. The present invention is by no means limited to these specific protocols or procedures.

Detection of Small Organics

The specific detection of small organic molecules depends on the acquisition of a recognition element specific for the target analyte, which is usually an antibody, however, it can be any molecule or structure capable of high-affinity, specific binding of the analyte. Antibodies have been used for the examples described below.

We have adapted two different approaches for the SPR detection/quantitation of small molecular weight analytes, a displacement assay (2-formats) and a competition assay.

For the displacement assay, two different implementations have been used. In the first, the sensor surface is derivatized with anti-target antibodies. The antibodies on the sensor surface are then "loaded" with a large reporter group (e.g., protein) to which target molecules have been covalently attached. Free analyte then displaces the bound target-conjugated reporter group at a rate that is proportional to the concentration of analyte. The second implementation involves attachment of the target to the sensor surface either as a target-protein conjugate or directly linked to the GBP foundation layer. Antibodies are then bound to the immobilized target molecules. Free target displaces the bound antibodies at rates proportional to the concentration of analyte. Antibodies with moderate affinities for analyte work best for this approach. It is possible to design fluidics where there is little consumption of antibodies using this approach. We have used this approach for the detection of dinitrophenol (DNP)-lysine and domoic acid, the amnesic shell fish poison in the low micromolar range of concentrations.

For the competition assay, an initial rate of antibody binding to immobilized target is established, then analyte is introduced directly into the antibody feed stream or preincubated with antibodies prior to flow through the SPR detection system. This approach has the advantage of a high level of sensitivity, especially if used with very high affinity antibodies. It has a disadvantage of consuming some antibody reagent. The range of sensitivity can be set by varying the concentration of the antibody feed stream. For the highest level of sensitivity, it requires the setting of the antibody concentration in the feed stream to a level that provides a low but detectable rate of antibody binding to the target immobilized on the sensor surface. We have used this protocol for the detection of cortisol, domoic acid and analyte conjugated to proteins used to generate the specific antibodies.

Detection of Protein Toxins

Protein toxins are of sufficient size to detect directly by SPR. A binding event generates a binding curve with an initial rate of binding that is proportional to the concentration of analyte. For *Staphylococcus* enterotoxin B binding to the portable Spreeta-based system, the current lower limit of detection (LOD) is approximately 100 pM. Using this protocol, we have detected the A chain of ricin and botulinum toxoid A (denatured botulinum toxin A). We have also used this same general protocol to test the suitability of the Spreeta based system for deployment in unattended air vehicles (UAVs) using the non-toxic proteins ovalbumin and horse radish peroxidase (Naimushin, Spinelli, Soelberg, Mann, Chinowsky, Kauffinan, Yee, Furlong, Airborne analyte detection with an aircraft-adapted surface plasmon resonance (SPR) sensor system. Sens Actuators, Vol. 104 pp. 237-248, 2005).

Detection of Low Concentration Analytes and Verification of Analyte Detection

It is important to avoid false positives when monitoring for toxic agents. The same approach that is used to detect low levels of analytes can be used to both amplify detection signals and verify that a specific analyte was detected to a high level of certainty. Once a putative detect signal has been observed, a second antibody with specificity for a different target epitope than was used to capture the analyte is flowed through the sensor system. Specific binding of this second antibody both verifies that the target analyte was bound and at the same time amplifies the original signal. It is also possible to design protocols with multiple steps of amplification when the concentration of analyte is very low. For example if a mouse monoclonal antibody is used on the sensor surface as the target capture antibody, rabbit polyclonal antibodies to the same target can be used to provide a significant amplification to the first signal. If this signal is still small, goat anti-rabbit antibodies can provide a second step of amplification. A third stage of amplification can be achieved with donkey anti-goat antibodies if necessary and so on. Having a dedicated reference channel with an antibody with a non-target specificity is very important to detect any non-specific binding that might occur. Using this approach, as noted above, we have been able to detect SEB at a level of 100 pM.

Detection of Viruses, Microbes and Spores.

The same protocols that are used for protein detection may be used to detect larger target analytes such as viruses, microbes and spores. Again, to avoid false positives, or to speciate the bound target, secondary antibodies with specificity for different target epitopes are used. For example, a general antibody for *Salmonella* strains could be used as the capture antibody on the sensor surface and when a signal is detected, antibodies specific for different strains can be used to identify the specific serological strain of organisms bound on the sensor surface. The speciation step will also provide amplification of the original signal.

E. Conclusion

The true scope the present invention is not limited to the presently preferred or illustrative embodiments disclosed herein. For example, the foregoing disclosure of embodiments of cartridge-based and portable SPR sensing systems includes explanatory terms, such as portable, cartridge-based, and the like, which should not be construed so as to limit the scope of protection of the following claims, or to otherwise imply that the inventive aspects of the system are limited to the particular methods and apparatus disclosed. Moreover, as will be understood by those skilled in the art, many of the inventive aspects disclosed herein may be applied in location systems that are not based on SPR techniques. For example, the processes by which the systems described herein detect the presence of malicious or dangerous target chemical and/or biological agents can be applied to detect other types of compounds, i.e., other than those discussed herein. Similarly, the invention is not limited to systems employing flowcells constructed as described above, nor to systems employing electronic or fluidic subsystems meeting all of the particulars described above. The various elements and subsystems are, in some cases, programmable data collection and processing devices that could take a variety of forms without departing from the inventive concepts disclosed herein. Given the rapidly declining cost of digital signal processing and other processing functions, it is easily possible, for example, to transfer the processing for a particular function from one of the functional elements described herein to another functional element without changing the inventive operation of the system. In many cases, the place of implementation (i.e., the functional element) described herein is merely a designer's preference and not a hard requirement. Accordingly, except as they may be expressly so limited, the scope of protection of the following claims is not intended to be limited to the specific embodiments described above.

What is claimed:

1. A portable surface plasmon resonance (SPR) sensing system, comprising:
    a portable housing; and
    sensing means for detecting the presence of predefined agents in a fluid medium using SPR, wherein at least a portion of said sensing means is contained within said portable housing;
    wherein said sensing means comprises an electrical system and a fluidics system;
    wherein said electrical system comprises an air pump for pressurizing said fluidics system, and a peristaltic pump; and
    wherein said sensing means further comprises a plurality of multi-channel sensor elements and means for configuring said sensor elements in a flowcell to permit the flow of a sample fluid into contact with each of said multi-channel sensor elements.

2. A system as recited in claim 1, wherein said fluidics system comprises an injection port; a first valve in fluid communication with the injection port; a pressurized buffer reservoir; a sample loop in fluid communication with the buffer reservoir; a flowcell in fluid communication with said sample loop; a second valve in fluid communication with said flowcell; and a waste reservoir in fluid communication with said second valve.

3. A system as recited in claim 2, further comprising a degasser in fluid communication with the sample loop.

4. A portable surface plasmon resonance (SPR) sensing system, comprising:
    a portable housing; and
    sensing means for detecting the presence of predefined agents in a fluid medium using SPR, wherein at least a portion of said sensing means is contained within said portable housing;
    wherein said sensing means comprises an electrical system and a fluidics system;
    wherein said electrical system comprises at least one SPR sensor, an air pump for pressurizing said fluidics system, and a peristaltic pump;
    wherein said electrical system further comprises a digital signal processor (DSP), a temperature controller, an air pump, and a peristaltic pump;
    wherein said fluidics system comprises an injection port; a first valve in fluid communication with the injection port; a pressurized buffer reservoir; a sample loop in fluid communication with the buffer reservoir; a flowcell in fluid communication with said sample loop; a second valve in fluid communication with said flowcell; and a waste reservoir in fluid communication with said second valve; and
    wherein said peristaltic pump is situated between said flowcell and said waste reservoir; said air pump is arranged so as to pressurize said buffer; and said SPR sensor is coupled to said flowcell so as to place a sample fluid in said flowcell in contact with said SPR sensor.

5. A system as recited in claim 4, further comprising a degasser in fluid communication with said sample loop and said flowcell, said degasser comprising a gas-permeable hydrophobic hollow fiber, wherein bubbles and dissolved gases are able to exit through pores in walls of the hollow fiber; and pressure sensors disposed at opposite ends of said hollow fiber.

6. A system as recited in claim 4, further comprising a concentrator in fluid communication with said sample loop and said flow cell.

7. A system as recited in claim 4, wherein said fluidics system further comprises a third valve in fluid communication with said sample loop.

8. A system as recited in claim 4, wherein said electrical system further comprises a digital signal processor (DSP).

9. A system as recited in claim 4, wherein said electrical system comprises a plurality of multi-channel SPR sensors.

10. A system as recited in claim 1, wherein said system comprises a disposable cartridge constructed to be removably inserted into said housing, said cartridge containing portions of said sensing means.

11. A portable surface plasmon resonance (SPR) sensing system, comprising: a portable housing and sensing means for detecting the presence of predefined agents in a fluid medium using SPR, wherein at least a portion of said sensing means is contained within said portable housing; wherein said sensing means comprises an electrical system and a fluidics system; wherein said electrical system comprises at least one SPR sensor, an air pump for pressurizing said fluidics system, and a peristaltic pump; wherein said system further comprises a disposable cartridge constructed to be removably inserted into said housing, said cartridge containing portions of said sensing means; and wherein said sensing means further comprises: a base unit electrical system and a base unit fluidics system contained within said base unit housing; and a cartridge electrical system and a cartridge fluidics system contained within said disposable cartridge;

and wherein said disposable cartridge comprises a thermally insulating plastic casing; a sample injection port coupled to said cartridge housing; a plurality of SPR sensors contained within said casing; and at least one battery contained within said casing, said at least one battery providing power for electrical components contained in the cartridge and the base unit housing when the cartridge is mated with the base unit.

12. A system as recited in claim 2, wherein said first and second valves are electronically-controllable zero dead-volume valves.

13. A system as recited in claim 4, wherein said first and second valves are electronically-controllable zero dead-volume valves.

14. A system as recited in claim 2, wherein a flow channel leading to said flow cell is characterized by a volume that is designed in accordance with the flow rate to provide a desired time in which a sample fluid reaches said flow cell.

15. A system as recited in claim 4, wherein a flow channel leading to said flow cell is characterized by a volume that is designed in accordance with the flow rate to provide a desired time in which a sample fluid reaches said flow cell.

16. A portable surface plasmon resonance (SPR) sensing system, comprising:
   a portable housing; and
   sensing means for detecting the presence of predefined agents in a fluid medium using SPR, wherein at least a portion of said sensing means is contained within said portable housing;
   wherein said sensing means comprises an electrical system and a fluidics system;
   wherein said electrical system comprises at least one SPR sensor, an air pump for pressurizing said fluidics system, and a peristaltic pump;
   said electrical system further comprising a plurality of multi-channel SPR sensors, an air pump for pressurizing said fluidics system, a peristaltic pump, and a temperature control system;
   said fluidics system comprising an injection port; a first zero dead-volume valve in fluid communication with the injection port; a pressurized buffer reservoir; a sample loop in fluid communication with the buffer reservoir; a flowcell in fluid communication with said sample loop; a second zero dead-volume valve in fluid communication with said flowcell; a waste reservoir in fluid communication with said second valve; and a degasser in fluid communication with the sample loop; and
   wherein said peristaltic pump is situated between said flowcell and said waste reservoir, and said SPR sensors are coupled to said flowcell so as to place a sample fluid in said flowcell in contact with said SPR sensors.

17. A system as recited in claim 16, wherein said system comprises a disposable cartridge constructed to be removably inserted into said housing, said cartridge containing portions of said electrical and fluidics systems.

18. A system as recited in claim 16, wherein a flow channel leading to said flow cell is characterized by a volume that is designed in accordance with the flow rate to provide a desired time in which a sample fluid reaches said flow cell.

19. A cartridge-based surface plasmon resonance (SPR) sensing system, comprising:
   a portable base unit housing;
   a disposable cartridge constructed to be removably mated with said housing;
   a base unit electrical system contained within said base unit housing;
   a cartridge electrical system contained within said cartridge;
   a base unit fluidics system contained within said base unit housing; and
   a cartridge fluidics system contained within said cartridge;
   wherein said base unit and cartridge electrical and fluidics systems are arranged for detecting the presence of predefined agents in a fluid medium using SPR.

20. A system as recited in claim 19, wherein said cartridge comprises a cartridge housing; a sample injection port coupled to said cartridge housing; a plurality of SPR sensors contained within said cartridge housing; and at least one battery contained within said cartridge housing, said at least one battery providing power for electrical components contained in the cartridge housing and the base unit housing when the cartridge housing is mated with the base unit housing.

21. A system as recited in claim 20, wherein said cartridge further comprises heat sinking means for equilibrating the temperature of the SPR sensors, and for equilibrating the temperature of a fluid stream within said cartridge.

22. A system as recited in claim 21, wherein said heat sinking means includes a means for mating with a heater/cooler mechanism in said base unit housing.

23. A system as recited in claim 22, wherein said cartridge further comprises a printed-circuit board that provides a physical frame for the cartridge and electrical connections to said at least one battery and SPR sensors.

24. A system as recited in claim 23, wherein said cartridge housing comprises a thermally insulating plastic casing forming external surfaces of the cartridge housing.

25. A system as recited in claim 20, wherein said cartridge fluidics system enables a user to inject a sample into the cartridge and comprises a means for preconditioning the sample, including performing degassing and temperature equilibration, and for flowing the injected sample over the SPR sensor surfaces at a controlled rate.

26. A system as recited in claim 25, wherein said cartridge fluidics system further comprises a silicone molded flowcell that provides a single flow channel covering all sensors in series.

27. A system as recited in claim 26, wherein said cartridge fluidics system further comprises aluminum front and back plates for aligning said flowcell to the SPR sensors and for equilibrating the temperature of liquid flowing in said flowcell.

28. A system as recited in claim 25, wherein said cartridge fluidics system further comprises a check valve in fluid communication with said sample injection port.

29. A system as recited in claim 25, wherein said cartridge fluidics system further comprises a sample loop in fluid communication with a pressurized buffer reservoir.

30. A system as recited in claim 25, wherein said cartridge fluidics system further comprises a waste reservoir for collecting liquid waste.

31. A system as recited in claim 25, wherein said cartridge fluidics system further comprises flow metering means including silicone peristaltic tubing and valves, and means for mating with a peristaltic pump rotor in said base unit housing.

32. A system as recited in claim 25, wherein said cartridge fluidics system further comprises an externally actuated valve that prevents fluid flow while said cartridge is not mated with said base unit.

33. A system as recited in claim 25, wherein said cartridge fluidics system further comprises a hollow-fiber degasser.

34. A system as recited in claim 25, wherein said cartridge fluidics system further comprises a hollow-fiber concentrator.

35. A system as recited in claim 33 or 34, wherein said cartridge fluidics system further comprises surface-mount pressure sensors mounted at opposite ends of said hollow-fiber degasser.

36. A system as recited in claim 19, wherein said cartridge comprises:
a cartridge housing comprising a thermally insulating plastic casing;
a sample injection port coupled to said cartridge housing;
a plurality of SPR sensors contained within said cartridge housing;
at least one battery contained within said cartridge housing, said at least one battery providing power for electrical components contained in the cartridge housing and the base unit housing when the cartridge housing is mated with the base unit housing;
heat sinking means for equilibrating the temperature of the SPR sensors, and for equilibrating the temperature of a fluid stream within said cartridge; and
a printed-circuit board that provides a physical frame for the cartridge and electrical connections to said at least one battery and SPR sensors.

37. A system as recited in claim 36, wherein said cartridge fluidics system comprises:
a silicone molded flowcell that provides a single flow channel covering all SPR sensors in series;
a means for preconditioning an injected sample, including performing degassing and temperature equilibration, and for flowing the injected sample over the SPR sensor surfaces at a controlled rate;
aluminum front and back plates for aligning said flowcell to the SPR sensors and for equilibrating the temperature of liquid flowing in said flowcell;
a check valve in fluid communication with said sample injection port;
a sample loop in fluid communication with a pressurized buffer reservoir;
a waste reservoir for collecting liquid waste;
flow metering means including silicone peristaltic tubing and valves, and means for mating with a peristaltic pump rotor in said base unit housing;
an externally actuated valve that prevents fluid flow while said cartridge is not mated with said base unit;
a hollow-fiber degasser; and
first and second surface-mount pressure sensors mounted at opposite ends of said hollow-fiber degasser.

38. A disposable cartridge constructed to be removably mated with a base unit of a surface plasmon resonance (SPR) sensing system, comprising:
a cartridge housing;
a sample injection port coupled to said cartridge housing;
a cartridge electrical system contained within said cartridge housing, including a plurality of SPR sensors;
a cartridge fluidics system contained within said cartridge housing;
at least one battery contained within said cartridge housing, said at least one battery providing power for electrical components of said cartridge electrical system; and
heat sinking means for equilibrating the temperature of the SPR sensors, and for equilibrating the temperature of a fluid stream within said cartridge fluidics system.

39. A disposable cartridge as recited in claim 38, wherein said cartridge fluidics system comprises:
a flowcell that provides a single flow channel covering said SPR sensors; and
a means for degassing an injected sample and for flowing the injected sample over the SPR sensor surfaces at a controlled rate.

40. A disposable cartridge as recited in claim 38, wherein said cartridge fluidics system further comprises:
aluminum front and back plates for aligning said flowcell to the SPR sensors and for equilibrating the temperature of liquid flowing in said flowcell;
a check valve in fluid communication with said sample injection port;
a pressurized buffer reservoir;
a sample loop in fluid communication with said pressurized buffer reservoir; and
a waste reservoir for collecting liquid waste.

41. A disposable cartridge as recited in claim 39, wherein said cartridge fluidics system further comprises:
flow metering means including peristaltic tubing and valves;
an externally actuated valve that prevents fluid flow while said cartridge is not mated with said base unit;
first and second surface-mount pressure sensors operatively coupled to said means for degassing.

42. A disposable cartridge as recited in claim 39, wherein said means for degassing includes a hollow-fiber degasser.

43. A disposable cartridge as recited in claim 39, further comprising an in-line hollow fiber concentrator in fluid communication with said cartridge fluidics system.

44. A disposable cartridge as recited in claim 38, wherein said cartridge housing comprises a thermally insulating casing.

45. A method for performing real-time monitoring of biological and/or chemical agents, comprising the steps of:
preparing a portable surface plasmon resonance (SPR) sensing system for detection of at least one target agent, wherein said at least one target agent is a member of a predetermined group consisting of nerve agents, small organics, toxic proteins, viruses, spores, microbes and environmental pollutants, and said SPR sensing system includes a plurality of multi-channel sensor elements;
configuring said sensor elements into a flowcell and coupling said flowcell with said portable SPR sensing system;
transporting said portable SPR sensing system to a monitoring location;
injecting an analyte into said portable SPR sensing system so as to cause said analyte to come into contact with said sensor elements; and
employing said portable SPR sensing system to detect said at least one target agent.

46. A method as recited in claim 45, wherein each said sensor element comprises a gold surface, and wherein the step of preparing the SPR sensing system comprises attaching a fusion protein to the gold surface and then releasing an alkaline phosphatase domain so as to effect a peptide foundation layer with free carboxyl and amino groups.

47. A method as recited in claim 45, wherein each said sensor element comprises a gold surface, and wherein the step of preparing the SPR sensing system comprises directly fusing a gold binding domain to receptor molecules.

48. A method as recited in claim 46, wherein said free carboxyl and amino groups are used for coupling of antibodies.

49. A method as recited in claim 46, wherein said free carboxyl and amino groups are used for coupling of receptors.

50. A method as recited in claim 46, wherein said free carboxyl and amino groups are used for coupling of recognition elements.

51. A method as recited in claim 46, wherein said free carboxyl and amino groups are used for coupling of antigens.

52. A method as recited in claim 46, wherein said peptide foundation layer serves to passivate the gold surface against non-specific binding of non-target analytes.

53. A method as recited in claim 45, wherein said method is used for the detection of small organic molecules.

54. A method as recited in claim 53, comprising the use of a displacement assay.

55. A method as recited in claim 54, wherein said use of a displacement assay comprises derivatizing said sensor surface with anti-target antibodies.

56. A method as recited in claim 55, further comprising loading said anti-target antibodies with a receptor group to which target molecules have been covalently attached.

57. A method as recited in claim 53, comprising the use of a competition assay.

58. A method as recited in claim 57, wherein said use of a competition assay comprises attachment of target molecules to the sensor surface as a target-protein conjugate.

59. A method as recited in claim 58, wherein said use of a competition assay comprises attachment of target molecules to the sensor surface followed by binding of antibodies to said target molecules.

60. A method as recited in claim 45, wherein said method is used for the detection of protein toxins.

61. A method as recited in claim 45, wherein said method is used for the detection of low concentration analytes and verification of analyte detection, and comprises observing a first putative detection signal, and then causing to flow through the sensor system a second antibody with specificity for a different target epitope, whereby specific binding of the second antibody effectively verifies that the target analyte was bound and amplifies the first signal.

62. A method as recited in claim 45, wherein the step of preparing the SPR sensing system comprises releasing an alkaline phosphatase domain so as to effect a peptide foundation layer with free carboxyl and amino groups.

* * * * *